United States Patent
Bolikal et al.

(10) Patent No.: US 10,717,810 B2
(45) Date of Patent: Jul. 21, 2020

(54) POLYMERIC BIOMATERIALS DERIVED FROM MONOMERS COMPRISING HYDROXYACIDS AND PHENOL COMPOUNDS AND THEIR MEDICAL USES

(71) Applicants: Rutgers, The State University of New Jersey, New Brunswick, NJ (US); Reva Medical, Inc., San Diego, CA (US)

(72) Inventors: Durgadas Bolikal, Edison, NJ (US); Joachim B. Kohn, Piscataway, NJ (US); Lioubov Kabalnova, San Diego, CA (US)

(73) Assignees: RUTGERS, THE STATE UNIVERSITY OF NEW JERSEY, New Brunswick, NJ (US); REVA MEDICAL, INC., San Diego, CA (US)

( * ) Notice: Subject to any disclaimer, the term of this patent is extended or adjusted under 35 U.S.C. 154(b) by 0 days.

(21) Appl. No.: 16/439,232

(22) Filed: Jun. 12, 2019

(65) Prior Publication Data

US 2019/0292312 A1  Sep. 26, 2019

Related U.S. Application Data

(62) Division of application No. 14/454,073, filed on Aug. 7, 2014, now Pat. No. 10,329,379.

(60) Provisional application No. 61/863,216, filed on Aug. 7, 2013.

(51) Int. Cl.
| | |
|---|---|
| *C08G 63/08* | (2006.01) |
| *C08G 63/64* | (2006.01) |
| *A61L 31/14* | (2006.01) |
| *A61L 31/18* | (2006.01) |
| *C08G 63/19* | (2006.01) |
| *C08G 64/02* | (2006.01) |
| *C08G 64/16* | (2006.01) |
| *A61L 31/06* | (2006.01) |
| *A61L 31/16* | (2006.01) |
| *C08G 63/91* | (2006.01) |
| *C08G 79/025* | (2016.01) |
| *C08G 79/04* | (2006.01) |

(52) U.S. Cl.
CPC .............. *C08G 63/08* (2013.01); *A61L 31/06* (2013.01); *A61L 31/148* (2013.01); *A61L 31/16* (2013.01); *A61L 31/18* (2013.01); *C08G 63/19* (2013.01); *C08G 63/64* (2013.01); *C08G 63/912* (2013.01); *C08G 64/0208* (2013.01); *C08G 64/0233* (2013.01); *C08G 64/1608* (2013.01); *C08G 64/1633* (2013.01); *C08G 79/025* (2013.01); *C08G 79/04* (2013.01); *A61L 2300/40* (2013.01); *A61L 2300/41* (2013.01); *A61L 2300/412* (2013.01); *A61L 2300/416* (2013.01)

(58) Field of Classification Search
CPC ..................................................... C08G 63/08
See application file for complete search history.

(56) References Cited

U.S. PATENT DOCUMENTS

| | | | |
|---|---|---|---|
| 5,099,060 A | 3/1992 | Kohn et al. | |
| 5,216,115 A | 6/1993 | Kohn et al. | |
| 5,463,013 A | 10/1995 | Tokuda et al. | |
| 5,658,995 A | 8/1997 | Kohn et al. | |
| 5,665,831 A | 9/1997 | Neuenschwander et al. | |
| 5,916,998 A | 6/1999 | Ferruti et al. | |
| 6,120,491 A | 9/2000 | Kohn et al. | |
| 6,475,477 B1 | 11/2002 | Kohn et al. | |
| 7,649,150 B2 | 1/2010 | Masuda | |
| 8,252,887 B2 | 8/2012 | Bolikal et al. | |
| 8,476,399 B2 | 7/2013 | Bolikal et al. | |
| 2005/0106119 A1 | 5/2005 | Brandom et al. | |
| 2006/0024266 A1 | 2/2006 | Brandom et al. | |
| 2006/0034769 A1 | 2/2006 | Kohn et al. | |
| 2009/0156629 A1 | 6/2009 | Zhao et al. | |
| 2010/0234555 A1 | 9/2010 | Bolikal et al. | |
| 2013/0203713 A1 | 8/2013 | Kohn et al. | |

FOREIGN PATENT DOCUMENTS

| | | |
|---|---|---|
| JP | H09-025258 | 1/1997 |
| JP | 2008509722 A | 4/2008 |
| JP | 2009510212 A | 3/2009 |
| WO | 2011142504 A1 | 11/2011 |
| WO | 2013116804 A2 | 8/2013 |

OTHER PUBLICATIONS

Lu et al. Journal of Asian Natural Products Research, 2009, 11, 397-400 (Year: 2009).*
Lu et al. Fitoterapia 2012, 83, 737-741 (Year: 2012).*
CAS Registry No. 372118-62-2, which entered STN on Nov. 28, 2001 (Year: 2001).*
CAS Registry No. 259257-10-8, which entered STN on Mar. 17, 2000 (Year: 2000).*
Bodanszky and Bodanszky, "Practice of Peptide Synthesis," Springer-Verlag, New York, 1984 (Synopsis).
Cordova et al, "Lipase-Catalyzed Formation of End-Functionalized Poly (Epsilon-Caprolactone) by Initiation and Termination Reactions," Polymer (Impact Factor: 3.77), Nov. 1999, vol. 40, No. 24, pp. 6709-6721 (Abstract).

(Continued)

*Primary Examiner* — Matthew P Coughlin
(74) *Attorney, Agent, or Firm* — Fox Rothschild LLP

(57) ABSTRACT

The present invention provides new classes of phenolic compounds derived from hydroxyacids and tyrosol or tyrosol analogues, useful as monomers for preparation of biocompatible polymers, and the biocompatible polymers prepared from these monomeric hydroxyacid-phenolic compounds, including novel biodegradable and/or bioresorbable polymers. These biocompatible polymers or polymer compositions with enhanced bioresorbabilty and processability are useful in a variety of medical applications, such as in medical devices and controlled-release therapeutic formulations. The invention also provides methods for preparing these monomeric hydroxyacid-phenolic compounds and biocompatible polymers.

11 Claims, No Drawings

(56) References Cited

OTHER PUBLICATIONS

Elias, et al., "Polyesters by Thionyl Chloride Activted Polycondensation," Makromol Chem, 1981, vol. 182, pp. 681-686 (Abstract).
Greene and Wuts, "Protective Groups in Organic Synthesis," John Wiley & Sons, New York, 1999, 3rd ed. (Abstract).
Higashi et al., "Preparation of Polyaryl Esters by a New Direct Polycondensation Reaction With Arylsulfonyl Chlorides in Pyridine," J. Polym Sci: Poly Chem Ed, 1983, vol. 21, No. 11, pp. 3233-3239 (Absract).
IUPAC-IUB Commission, "IUPAC-IUB Commission of Biochemical Nomenclature. Abbreviated nomenclature of synthetic polypeptides (polymerized amino acids). Revised recommendations (1971)," Biochem 1972, vol. 11, No. 5, pp. 942-944 (Abstract).
Laurencin et al., "Poly(anhydride) Administration in High Doses In Vivo: Studies of Biocompatibility and Toxicology," J. Biomed Mater Res, 1990, vol. 24, No. 11, pp. 1463-1481 (Abstract).
Moore et al., "Room Temperature Polyesterification," Macromol, 1990, vol. 23, No. 1, pp. 65-70.
Schnell, "Chemistry and Physics of Polycarbonates," Interscience, New York, 1964 (Abstract).
HCL: "An Overview of the Plastic Material Selection Process for Medical Devices", Feb. 2013, pp. 1-26.
Dow: Calibre Polycarbonate Resins, Jul. 2001, pp. 1-48.
Lu, et al: "Aromatic Compounds from Endophytic Fungus *Colletotrichum* sp. L10 of *Cephalotaxus hainanensis* Li", Fitoterapia, 2012, vol. 83, pp. 737-741.
Chlipala, et al: "Nhatrangins A and B, Aplysiatoxin-Related Metabolites from the Marine *Cyanobacterium lyngbya majuscula* from Vietnam", J. Nat. Prod., 2010, vol. 73, pp. 784-787.
Dewitt, et al: "A Cascade Biodegradable Polymer Based on Alternating Cyclization and Elimination Reactions", J. Am. Chem. Soc, 2009, vol. 131, pp. 18327-18334.
Tanaka, Mamoru: Liquid Crystalline Polyurethane Polyurethanes Containing BIS-[p-oxymethylphenyl] Terephthalate, J. Macromol. Sci.-Chem., 1987, vol. A24, No. 7, pp. 777,785.
Byrne, et al: "Biodegradable Polymer Versus Permanent Polymer Drug-Eluting Stents and Everolimus—Versus Sirolimus-Eluting Stents in Patients with Coronary Artery Disease", Journal of the American College of Cardiology, Nov. 13, 2011, vol. 58, No. 13, pp. 1325-1331.
Chen, et al: "Self-Immolative Polymers Containing Rapidly Cyclizing Spacers Toward Rapid Depolymerization Rates", Macromolecules, 2012, vol. 45, pp. 7364-7374.

* cited by examiner

POLYMERIC BIOMATERIALS DERIVED FROM MONOMERS COMPRISING HYDROXYACIDS AND PHENOL COMPOUNDS AND THEIR MEDICAL USES

CROSS-REFERENCE TO RELATED APPLICATION

The present application is a Divisional Application of U.S. Non-Provisional application Ser. No. 14/454,073, filed Aug. 7, 2014, which claims the benefit of priority under 35 USC 119(e) of U.S. Provisional Application No. 61/863,216 filed on Aug. 7, 2013. The entire disclosures of the applications noted above are incorporated herein by reference.

FIELD OF THE INVENTION

The present invention relates to new classes of monomeric phenol compounds useful for preparation of biocompatible polymers, and biocompatible polymers prepared therefrom, including novel biodegradable and/or bioresorbable polymers. These polymers, while not limited thereto, may be adapted for radio-opacity and are useful for medical device applications and controlled release therapeutic formulations.

BACKGROUND OF THE INVENTION

The rapidly evolving field of bioengineering has created a demand for a diverse library of different types of polymers offering a wide variety of choice of physical, mechanical, chemical and physiological properties. It is desirable that libraries of many different materials be available so that the specific polymer properties can be optimally matched with the requirements of the specific applications under development.

Examples of polymers suitable for various bioengineering applications include those described in U.S. Pat. Nos. 5,099,060; 5,665,831; 5,916,998 and 6,475,477, along with the polymers described in U.S. Patent Publication Nos. 2006/0024266 and 2006/0034769. There are numerous applications in which it is considered desirable for an implanted medical device to maintain its integrity and performance characteristics for extended periods of time, even under demanding mechanical conditions such as repeated mechanical flexure. Although many types of bioresorbable and/or biodegradable polymers are known, in most of these polymers diphenolic monomers are prepared by linking two suitably protected tyrosine molecules or tyrosine analogs via an amide linkage. These amide linkages do not degrade hydrolytically under physiological conditions and therefore the monomers which have low solubility in water, dissolve very slowly. Further, due to hydrogen bonding of amide hydrogen the melt viscosity of the polymers derived from these monomers is very high, which makes thermal processing more difficult. In addition, bioresorbtion and/or biodegradation tend to alter mechanical properties in unpredictable ways that are not necessarily linearly related to each other.

Thus, there continues to be a need for biocompatible polymers having desirable bioresorbability and biodegradability, good processability under thermal conditions, as well as the appropriate level of mechanical structural support necessary for medical device applications. There remains a need for nontoxic polycarbonates, polyarylates and other polymers having a moderate rate of bioerosion, suitable for use as tissue-compatible materials for biomedical uses.

SUMMARY OF THE INVENTION

The present invention addresses the foregoing need by providing new monomers useful for the preparation of the desired biocompatible polymers and various types of such polymers useful for making the implantable medical devices.

Hydroxyacid-phenolic compounds, such as tyrosyl lactates, tyrosyl glycolates and related compounds are a new class of diol monomer/macromers in which one of the hydroxy groups is aromatic (phenolic) and the other is aliphatic. These can be prepared, for example, by using tyrosol as the initiator for the ring opening reactions of cyclic reaction partners such as lactides, lactones and cyclic carbonates. Using such monomers as co-monomers together with other diphenolic monomers in condensation polymerizations provides rigidity and mechanical strength that is lacking in aliphatic-derived monomers and also allows degrees of flexibility and degradability that are desirable in bioresorbable polymers for medical uses.

The present invention broadly relates to hydroxyacid-phenolic monomers and bioerodible polymers synthesized using such monomers. In various embodiments, the hydroxyacid-phenolic monomers are derived from tyrosol and/or related analogs. In particular, one preferred aspect of the present invention is directed to bioerodible polycarbonates and polyarylates derived from the naturally occurring 4-(2-hydroxylethyl)phenol (or "tyrosol") and phosgene and/or biocompatible dicarboxylic acids.

One aspect the present invention is directed to biocompatible polymers comprising a repeating structural unit of the Formula

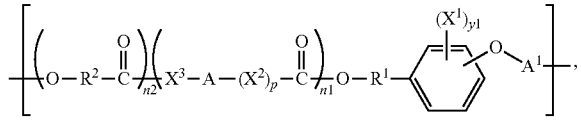

wherein
y1 is 0, 1, 2, 3, or 4;
$X^1$ is bromine (Br) or iodine (I);
$X^2$ and $X^3$ are independently selected from O, S and NR, where R is H or lower alkyl;
$R^1$ is selected from the group consisting of linear or branched $C_1$-$C_{12}$ alkylene;
A is selected from the group consisting of linear or branched $C_1$-$C_{24}$ alkylene;
$R^2$ is selected from the group consisting of linear or branched $C_1$-$C_{24}$ alkylene;
n1 and n2 are independently numbers from 0 to 100, and are average values which can be fractional, where the sum of n1 and n2 is at least 1;
p is zero or 1; and
$A^1$ is a linking group selected from:

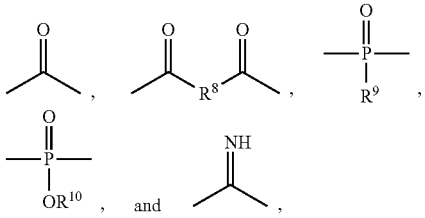

wherein $R^8$ is selected from a bond. $C_1$-$C_{30}$ alkylene, $C_2$-$C_{30}$ alkenylene, $C_2$-$C_{30}$ alkynylene; $C_1$-$C_{30}$ heteroalkylene, $C_2$-$C_{30}$ heteroalkenylene, $C_2$-$C_{30}$ heteroalkynylene, $C_7$-$C_{30}$ heteroalkylarylene, $C_8$-$C_{30}$ heteroalkenylarylene, $C_8$-$C_{30}$ heteroalkynylarylene, $C_7$-$C_{30}$ alkylarylene, $C_8$-$C_{30}$ alkenylarylene, $C_8$-$C_{30}$ alkynylarylene, and $C_2$-$C_{30}$ heteroarylene; and $R^9$ and $R^{10}$ are each independently selected from H, $C_1$-$C_{30}$ alkyl, $C_3$-$C_{30}$ heteroalkyl, $C_2$-$C_{30}$ alkenyl, $C_2$-$C_{30}$ alkynyl, $C_2$-$C_{30}$ heteroalkenyl, and $C_2$-$C_{30}$ heteroalkynyl;

wherein said alkyl and alkylene can be substituted with one or more of hydroxy, alkoxy, halogen, nitro, cyano, $CO_2R$, where R is defined above, phenyl, aryl, heteroaryl, cycloalkyl, mercapto, or alkylthio.

In a preferred embodiment, $R^2$ is CH—$R^3$, where $R^3$ is selected from hydrogen and $C_1$-$C_{23}$ alkyl.

Examples of the inventive polymers include polycarbonates, polyarylates, polyiminocarbonates, polyphosphazenes and polyphosphoesters.

Another aspect the present invention is directed to hydroxyacid-phenol compounds of formula:

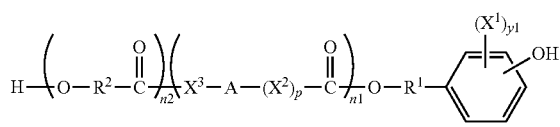

wherein
y1 is 0, 1, 2, 3, or 4;
$X^1$ is bromine (Br) or iodine (I);

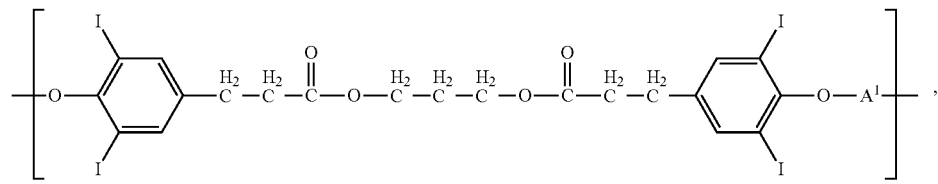

$X^2$ and $X^3$ are independently selected from O, S and NR, where R is H or lower alkyl;
$R^1$ is selected from the group consisting of linear or branched $C_1$-$C_{12}$ alkylene;
A is selected from the group consisting of linear or branched $C_1$-$C_{24}$ alkylene;
$R^2$ is selected from the group consisting of linear or branched $C_1$-$C_{24}$ alkylene;
n1 and n2 are independently numbers from 0 to 100, and are average values which can be fractional, where the sum of n1 and n2 is at least 1;
p is zero or 1; and
wherein said alkyl and alkylene can be substituted with one or more of hydroxy, alkoxy, halogen, nitro, cyano, $CO_2H$, $CO_2$-lower alkyl, phenyl, aryl, heteroaryl, cycloalkyl, mercapto, or alkylthio.

In a preferred embodiment, $R^2$ is CH—$R^3$, where $R^3$ is selected from hydrogen and $C_1$-$C_{23}$ alkyl.

Yet another aspect of the invention is directed to polymer compositions comprising a biocompatible polymer described herein.

One aspect of the invention is direct to medical devices comprising a biocompatible polymer described herein. In a preferred embodiment, the medical device is a stent.

Another aspect of the invention is direct to inventive biocompatible polymers further comprising a macromeric recurring unit, or a recurring unit of the formula:

wherein B is —O—$((CHR)_p$—O$)_q$—; each R is independently H or $C_1$ to $C_3$ alkyl; p and q are each independently an integer in the range of from 1 to 100; and $A^1$ is as defined above, independently from any other $A^1$; or a tyrosol recurring unit characterized by the formula:

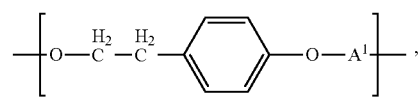

wherein $A^1$ is as defined above, independently from any other $A^1$; or an iodinated tyrosol recurring unit characterized by the formula:

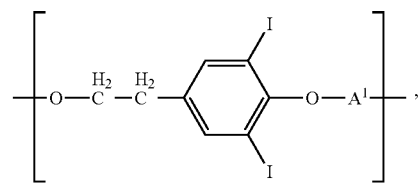

wherein $A^1$ is as defined above, independently from any other $A^1$; or an iodinated recurring unit characterized by the formula:

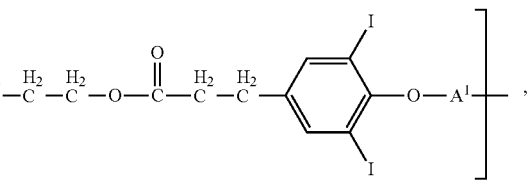

wherein $A^1$ is as defined above, independently from any other $A^1$.

These and other embodiments are described in greater detail below.

DETAILED DESCRIPTION OF PREFERRED EMBODIMENTS

To meet the need of versatile moldable biodegradable and biocompatible polymers made using relatively nontoxic monomeric starting materials, the present application describes a variety of such monomers and polymers prepared from these monomers.

One aspect of the invention is directed to a biocompatible polymer, comprising a recurring unit of formula:

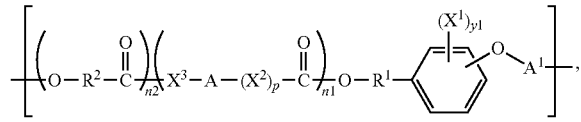

wherein
y1 is 0, 1, 2, 3, or 4; preferably 0, 1 or 2; or preferably 1 or 2; or preferably 2;

$X^1$ is a halogen; preferably bromine (Br) or iodine (I); more preferably iodine;

$X^2$ and $X^3$ are independently selected from O, S and NR, where R is H or lower alkyl; preferably $X^2$ and $X^3$ are O;

$R^1$ is selected from the group consisting of linear or branched $C_1$-$C_{12}$ alkylene; preferably $C_1$-$C_6$ alkylene; more preferably $C_1$-$C_4$ alkylene; most preferably $C_2$ alkylene;

A is selected from the group consisting of linear or branched $C_1$-$C_{24}$ alkylene; preferably $C_1$-$C_6$ alkylene; more preferably $C_1$-$C_6$ alkylene; still more preferably $C_2$-$C_4$ alkylene; most preferably $C_1$-$C_2$ alkylene;

$R^2$ is selected from the group consisting of linear or branched $C_1$-$C_{24}$ alkylene; preferably $C_1$-$C_{12}$ alkylene; more preferably $C_1$-$C_6$ alkylene; still more preferably $C_1$-$C_4$ alkylene; most preferably $C_1$-$C_2$ alkylene;

n1 and n2 are independently numbers from 0 to 100, preferably 0 to 20, more preferably 0 to 10, still more preferably 0 to 5, most preferably 0 to 2, and are average values which can be fractional, where the sum of n1 and n2 is at least 1;

p is zero or 1; and $A^1$ is a linking group selected from:

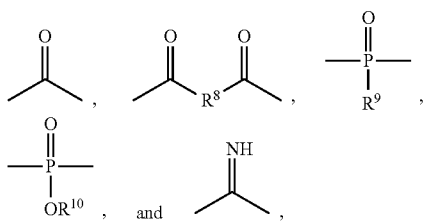

wherein $R^8$ is selected from a bond, $C_1$-$C_{30}$ alkylene, $C_2$-$C_{30}$ alkenylene, $C_2$-$C_{30}$ alkynylene; $C_1$-$C_{30}$ heteroalkylene, $C_2$-$C_{30}$ heteroalkenylene, $C_2$-$C_{30}$ heteroalkynylene, $C_7$-$C_{30}$ heteroalkylarylene, $C_8$-$C_{30}$ heteroalkenylarylene, $C_8$-$C_{30}$ heteroalkynylarylene, $C_7$-$C_{30}$ alkylarylene, $C_8$-$C_{30}$ alkenylarylene, $C_8$-$C_{30}$ alkynylarylene, and $C_2$-$C_{30}$ heteroarylene; and $R^9$ and $R^{10}$ are each independently selected from H, $C_1$-$C_{30}$ alkyl, $C_2$-$C_{30}$ heteroalkyl, $C_1$-$C_{30}$ alkenyl, $C_2$-$C_{30}$ alkynyl, $C_2$-$C_{30}$ heteroalkenyl, and $C_2$-$C_{30}$ heteroalkynyl;

wherein said alkyl and alkylene can be substituted with one or more of hydroxy, alkoxy, halogen, nitro, cyano, $CO_2R$, where R is defined above, phenyl, aryl, heteroaryl, cycloalkyl, mercapto, or alkylthio.

In one embodiment $R^1$ is $C_1$-$C_4$ alkylene. Preferably $R^1$ is —$CH_2CH_2$—.

In another embodiment, $A^1$ is carbonyl (C=O). In another embodiment $A^1$ is derived from a diacid and has the structure (O=C)—$R^8$—(C=O), with $R^8$ as defined above.

In one embodiment, n1 is zero and n2 is an average value between 0.5 and 6. Preferably n2 is an average value between 1 and 2.

In another embodiment the biocompatible polymer comprises recurring unit of formula:

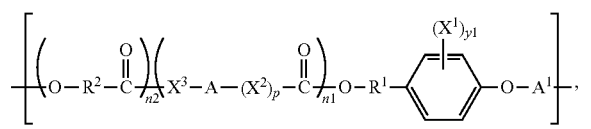

having the phenolic attachment at the para position of the phenyl ring, where the variables are defined above.

In another embodiment the biocompatible polymer comprises recurring unit of formula:

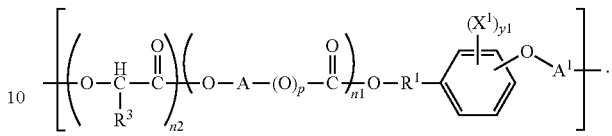

wherein $R^3$ is selected from the group consisting of hydrogen and linear or branched $C_1$-$C_{23}$ alkyl, and the other variables are defined above. In a preferred embodiment the recurring unit is of formula:

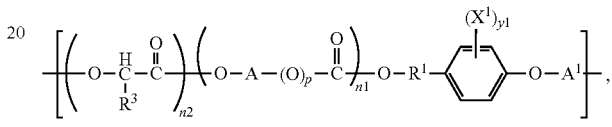

having the phenolic attachment at the para position of the phenyl ring, where the variables are defined above. Preferably $R^3$ is hydrogen or methyl. In a preferred embodiment, n2 is greater than zero and $R^3$ is methyl and the subunit is derived from L-lactic acid. In another preferred embodiment n2 is greater than zero and $R^3$ is methyl and the subunit is derived from D-lactic acid. In another preferred embodiment, n2 is greater than zero and $R^3$ is methyl and the subunit is derived from D,L-lactic acid.

In another aspect of the invention, the biocompatible polymer further comprises a recurring unit of the formula:

wherein B is —O—$((CHR)_p$—$O)_q$—; each R is independently H or $C_1$ to $C_3$ alkyl; p and q are each independently an integer in the range of from 1 to 100; and $A^1$ is as defined above, independently from any other $A^1$. Preferably R is H and p is 2, providing a poly(ethylene glycol) (PEG) recurring unit.

In another aspect of the invention, the biocompatible polymer further comprises a recurring unit of the formula:

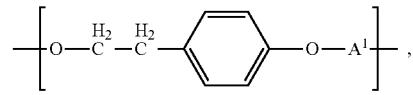

wherein $A^1$ is as defined above, independently from any other $A^1$.

In another aspect of the invention, the biocompatible polymer further comprises a recurring unit of the formula:

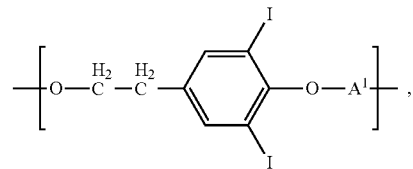

wherein $A^1$ is as defined above, independently from any other A.

In another aspect of the invention, the biocompatible polymer further comprises a recurring unit of the formula:

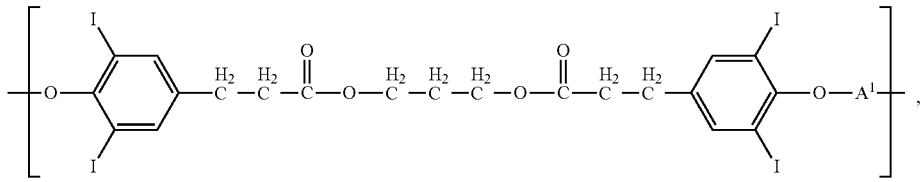

wherein $A^1$ is as defined above, independently from any other $A^1$.

A further aspect of the invention is directed to hydroxy-acid-phenol compounds of formula:

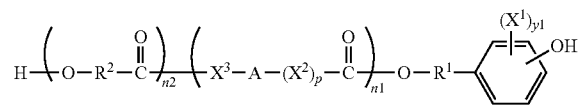

wherein
- y1 is 0, 1, 2, 3, or 4; preferably 0, 1 or 2; or preferably 1 or 2; or preferably 2;
- $X^1$ is a halogen; preferably bromine (Br) or iodine (I); more preferably iodine;
- $X^2$ and $X^3$ are independently selected from O, S and NR, where R is H or lower alkyl; preferably $X^2$ and $X^3$ are O;
- $R^1$ is selected from the group consisting of linear or branched $C_1$-$C_{12}$ alkylene; preferably $C_1$-$C_6$ alkylene; more preferably $C_1$-$C_4$ alkylene; most preferably $C_2$ alkylene;
- A is selected from the group consisting of linear or branched $C_1$-$C_{24}$ alkylene; preferably $C_1$-$C_{12}$ alkylene; more preferably $C_1$-$C_6$ alkylene; still more preferably $C_2$-$C_4$ alkylene; most preferably $C_3$ alkylene;
- $R^2$ is selected from the group consisting of linear or branched $C_1$-$C_{24}$ alkylene; preferably $C_1$-$C_{12}$ alkylene; more preferably $C_1$-$C_6$ alkylene; still more preferably $C_1$-$C_4$ alkylene; most preferably $C_1$-$C_2$ alkylene;
- n1 and n2 are independently numbers from 0 to 100, preferably 0 to 20, more preferably 0 to 10, still more preferably 0 to 5, most preferably 0 to 2, and are average values which can be fractional, where the sum of n1 and n2 is at least 1;
- p is zero or 1; and
- wherein said alkyl and alkylene can be substituted with one or more of hydroxy, alkoxy, halogen, nitro, cyano, $CO_2H$, CO-lower alkyl, phenyl, aryl, heteroaryl, cycloalkyl, mercapto, or alkylthio.

In one embodiment n1 is zero and n2 is an average value of 2. In another embodiment $X^1$=I and y1=2. Preferably $R^1$ is —$CH_2CH_2$— (tyrosol).

In another aspect of the invention, the hydroxyacid-phenol has the formula:

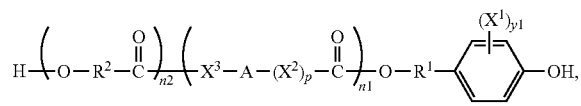

where the phenolic attachment is at the para position of the phenyl ring, and the variables are defined above.

In a further aspect of the invention, the hydroxyacid-phenol compound has the formula:

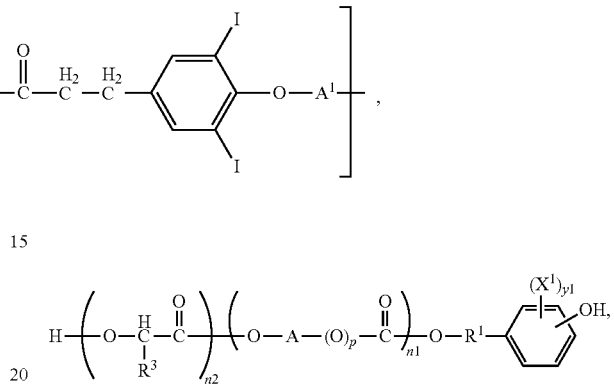

wherein $R^3$ is selected from the group consisting of hydrogen and linear or branched $C_1$-$C_{23}$ alkyl, and the other variables are defined as above. Preferably the hydroxyacid-phenol compound has the formula:

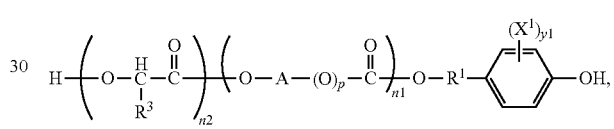

where the phenolic attachment is at the para position of the phenyl ring, and the variables are defined above.

In a preferred embodiment, $R^3$ is hydrogen or methyl. In one preferred embodiment, n2 is greater than zero and $R^3$ is methyl and the subunit is derived from L-lactic acid. In another preferred embodiment, n2 is greater than zero and $R^3$ is methyl and the subunit is derived from D-lactic acid. In still another preferred embodiment, n2 is greater than zero and $R^3$ is methyl and the subunit is derived from D,L-lactic acid.

One aspect of the invention is directed to polymer compositions comprising a biocompatible polymer described herein.

Another aspect of the invention is directed to a medical device comprising a biocompatible polymer described herein. In one embodiment, the medical device is a stent. The medical device can further comprise a biologically active compound. The biologically active compound can be selected from the group consisting of a chemotherapeutic agent, a non-steroidal anti-inflammatory, a steroidal anti-inflammatory, and a wound healing agent.

In one particular aspect this invention provides hydroxy-acid-phenolic monomers derived from a hydroxyalkylphenol having a generic structure of Formula (IV):

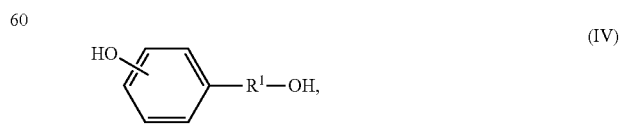

wherein $R^1$ is defined as above. $R^1$ is preferably $C_1$-$C_{12}$ alkylene, e.g., $C_1$-$C_4$ alkylene. More preferably $R^1$ is ethylene (—CH$_2$—CH$_2$—). Most preferably, the hydroxyalkylphenol is 4-(2-hydroxyethyl)phenol or 2-(4-hydroxyphenyl)ethanol, also known as "tyrosol", having the following structure:

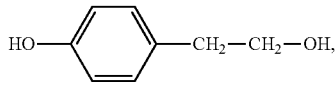

which is a natural product present in olive oil and white wine and has been shown to have both antioxidant and cardioprotective properties. The phenyl ring of tyrosol can be halogenated, and those skilled in the art will understand that teachings herein regarding tyrosol can be applied to such halogenated forms as well. Tyrosol can be converted into a hydroxyacid-phenolic monomer in several ways. It can be esterified with hydroxyacids, particularly alpha-hydroxyacids, to form a phenolic monomer with an ester linkage. These monomers can be introduced into polymers to control chain flexibility, as needed. Those skilled in the art will appreciate that use of ring halogenated compounds (e.g., halogenated tyrosol) provides the corresponding halogenated polymers.

The hydroxyacid-phenolic monomers described herein, can be polymerized using phosgene to form polycarbonates, or polymerized with dicarboxylic acids to obtain polyarylates. The hydroxyacid-phenolic monomers can also be copolymerized with other co-monomers, including diphenols (such as desaminotyrosyl tyrosine ethyl ester, DAT) and other dihydroxy compounds such as poly(ethylene glycol), polycaprolactone-diol, poly(trimethylene carbonate), polylactide and/or polyglycolide. Suitable co-monomers are disclosed in U.S. Pat. Nos. 8,252,887 and 8,476,399, the disclosures of which are incorporated herein by reference. The polymers can be made radio-opaque by introducing halogen, in particular iodine and/or bromine atoms, on the phenyl rings, or on other suitable sites of the monomers. Other optionally halogenated phenolic alcohols can be used in place of tyrosol, and other optionally halogenated hydroxy carboxylic acids can be used in place of glycolic acid and lactic acid.

In another aspect, the present invention provides a biocompatible polymer composition, comprising at least a first polymer component and a second polymer component. In an embodiment, the first polymer component comprises a number (n) of first recurring units of the hydroxyacid-phenolic compounds as set forth above, and the second polymer component comprises recurring units having a formula selected from the group consisting of the formula (IX), the formula (X), the formula (XI), and the formula (XII):

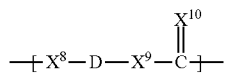 (IX)

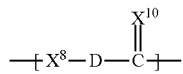 (X)

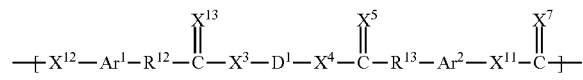 (XI)

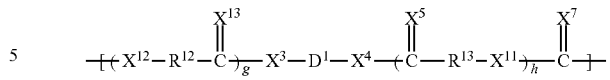 (XII)

wherein $X^3$, $X^4$, $X^5$, $X^7$, $X^8$, $X^9$, $X^{10}$, $X^{11}$, $X^{12}$ and $X^{13}$ are independently selected from the group consisting of O, S and NR$^{11}$, where R$^{11}$ is selected from hydrogen and an alkyl group containing from one to 30 carbon atoms;

Ar$^1$ and Ar$^2$ are phenyl rings optionally substituted with from one to four substituents independently selected from the group consisting of a halogen, a halomethyl, a halomethoxy, a methyl, a methoxy, a thiomethyl, a nitro, a sulfoxide, and a sulfonyl;

R$^{12}$ and R$^{13}$ contain from one to ten carbon atoms each and are independently selected from the group consisting of an optionally substituted alkylene, an optionally substituted heteroalkylene, an optionally substituted alkenylene, and an optionally substituted heteroalkenylene;

g and h in formula (XII) are each independently integers in the range of about 1 to about 500; and D and D$^1$ contain up to 24 carbon atoms and are independently selected from the group consisting of an optionally substituted alkylene, an optionally substituted heteroalkylene, an optionally substituted alkenylene and an optionally substituted heteroalkenylene;

or D, $X^8$ and $X^9$ in formula (IX) are selected so that HX$^8$-D-X$^9$H defines a hydroxyl endcapped macromer, a mercapto endcapped macromer or an amino endcapped macromer;

or D$^1$, $X^3$ and $X^4$ in formula (XI) are selected so that HX$^3$-D$^1$-X$^4$H defines a hydroxyl endcapped macromer, a mercapto endcapped macromer or an amino endcapped macromer. These, as well as other suitable polymer components and/or polymer phases are set forth in U.S. patent application Ser. No. 12/577,203, which is incorporated herein by reference.

In other aspects, the present invention provides copolymers that comprise any two or more of the recurring units described herein. For example, in an embodiment, the polymer comprises two or more recurring units selected from the group of recurring units represented by the formulae presented above. In another embodiment, the polymer comprises at least two recurring units resulting from the polymerization of any two or more monomers described herein.

In other aspects of the invention, the polymer comprises a backbone which is not naturally occurring. Alternatively and/or additionally, the polymer may comprise a backbone comprising at least one amino acid derivative.

A polymer comprising a recurring unit as described herein can be copolymerized with any number of other recurring units. In an embodiment, a polymer comprising a recurring unit of any one or more of the above formulae, further comprises a recurring unit of the formula (XIV):

 (XIV), wherein:

B in formula (XIV) is —O—((CHR)$_p$—O)$_q$—;

each R is independently H or C$_1$ to C$_3$ alkyl;

p and q are each independently an integer in the range of from about 1 to about 100; and A$^1$ is as defined above, independently from any other A.

In preferred embodiments, Formula (XIV) includes polyethylene glycol (PEG) recurring units (R=H and p=2), polyproplyene glycol (PPO) recurring units (p=2, and two adjacent R's=H and CH$_3$, respectively) and/or poly(trimethylene carbonate) (PTMC) recurring units (R=H, q=1, p=3 and

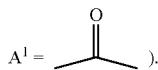).

In vivo, the polymer is expected to hydrolyze to release the original hydroxyacid-phenolic compound and diacid (polyarylate) or CO$_2$ (polycarbonate), thus forming nontoxic degradation products, provided that the monomeric starting materials are nontoxic. The toxicological concerns associated with polyarylates are met by using hydroxyacid-phenolic derived from tyrosol and dicarboxylic acids that are either metabolites or highly biocompatible compounds.

Another aspect of the present invention provides molded articles prepared from the polymers of the present invention.

Based on the foregoing, in certain embodiments of the biocompatible polymers described herein, A$^1$ is a carbonyl group having a structure of

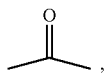, wherein the carbonyl group is derived from a phosgene starting material. This method is essentially the conventional method for polymerizing diols into polycarbonates. Suitable processes, associated catalysts and solvents are known in the art and are taught in, for example, Schnell, Chemistry and Physics of Polycarbonates, (Interscience, New York 1964), the teachings of which are incorporated herein by reference. Other methods adaptable for use to prepare the poly-carbonate and other phosgene-derived polymers of the present invention are disclosed in U.S. Pat. Nos. 6,120,491 and 6,475,477 the disclosures of which are incorporated by reference.

In another embodiment of the polymers described herein, A$^1$ is a group having the structure:

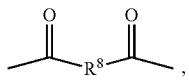, which is a recurring unit derived from a dicarboxylic acid starting material or monomer. When the monomer used to form the polymer is a hydroxyacid-phenolic compound, the hydroxyacid-phenol can be reacted with an aliphatic or aromatic dicarboxylic acid in the carbodiimide mediated process disclosed by U.S. Pat. No. 5,216,115 using 4-(dimethylamino)pyridinium p-toluene sulfonate (DPTS) as a catalyst. The disclosure of U.S. Pat. No. 5,216,115 is incorporated by reference, and particularly for the purpose of describing such polymerization methods. This process forms polymers with —O—C(=O)—R$^8$—C(=O)—O— linkages. R$^8$ may be selected so that the dicarboxylic acids employed as starting materials are either important naturally-occurring metabolites or highly biocompatible compounds. Aliphatic dicarboxylic acid starting materials therefore include the intermediate dicarboxylic acids of the cellular respiration pathway known as the Krebs Cycle. The dicarboxylic acids include α-ketoglutaric acid, succinic acid, fumaric acid and oxaloacetic acid (R$^8$ may be —CH$_2$—CH$_2$—C(=O)—, —CH$_2$—CH$_2$—, —CH=CH— and —CH$_2$—C(=O)—, respectively).

Yet another naturally occurring aliphatic dicarboxylic acid is adipic acid (R$^8$ is —(CH$_2$)$_4$—), found in beet juice. Still another biocompatible aliphatic dicarboxylic acid is sebacic acid (R$^5$ is —(CH$_2$)$_8$—), which has been studied extensively and has been found to be nontoxic as part of the clinical evaluation of poly(bis(p-carboxyphenoxy)propane-co-sebacic acid anhydride) by Laurencin et al., J. Biomed. Mater. Res., 24, 1463-81 (1990).

Other biocompatible aliphatic dicarboxylic acids include oxalic acid (R$^8$ is a bond), malonic acid (R$^5$ is —CH$_2$—), glutaric acid (R$^8$ is —(CH$_2$)$_3$—), pimelic acid (R$^8$ is —(CH$_2$)$_5$—), suberic acid (R$^8$ is —(CH$_2$)$_6$—) and azelaic acid (R$^8$ is —(CH$_2$)$_7$—). R$^8$ can thus represent —(CH$_2$)$_n$—, where n is between 0 and 8, inclusive. Among the suitable aromatic dicarboxylic acids are terephthalic acid, isophthalic acid and bis(p-carboxy-phenoxy) alkanes such as bis(p-carboxy-phenoxy) propane.

Preferred polymers comprise a recurring unit as described herein. Preferred polymers can contain combinations of derivatives of structural units selected from dicarboxylic acids, halogenated (e.g., iodinated or brominated) derivatives of desaminotyrosyl-tyrosine and poly(alkylene glycols), which exhibit desirable physicomechanical and physicochemical properties that are consistent with their use in fabrication of medical devices, including stents. For example, the stents described in accordance with preferred embodiments of the present invention: (a) are sufficiently radiopaque to be visible by conventional X-ray fluoroscopy; (b) are of sufficient strength to support medically relevant levels of radial compression within an artery or surrounding tissue; and/or (c) have a desirable resorption profile that may be adjusted to account for the needs of a range of applications requiring the presence of a stent for different lengths of time or for the elution of therapeutics.

Halogenation of the aromatic rings may be accomplished as described in the examples below, and by conventional methods as detailed in U.S. Pat. No. 6,475,477; herein incorporated in its entirety by reference and particularly for the purpose of describing methods of halogenating monomers. Preferred polymers are sufficiently halogenated to render the resulting polymers radiopaque, e.g., y1 in any of the formulae described herein may independently be 0, 1, 2, 3 or 4. Halogenation of aromatic rings is preferred. In an embodiment, y1 is at least one. Various other groups within the polymer may also be halogenated.

Monomer and Polymer Syntheses

The hydroxyacid-phenolic monomers of the invention are advantageously prepared by the reaction of a hydroxyalkylphenol having a generic structure of Formula (IV):

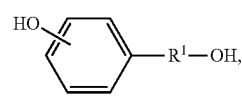

as described above, with a cyclic reaction partner preferably selected from the group consisting of cyclic dimers of alpha-hydroxyacids, lactones and cyclic carbonates (see Examples). Preferably the hydroxyalkylphenol is tyrosol (R$^1$=CH$_2$CH$_2$, with phenolic OH in the para-position). Cyclic dimers of alpha-hydroxyacids include, without limitation, glycolide and lactide. The lactide can be L,L-lactide, R,R-lactide, L,R-lactide, or racemic lactide, since the precursor lactic acid contains a chiral carbon atom. We have observed that reaction of tyrosol, and related hydroxyalkylphenols, with such cyclic reaction partners proceeds by exclusive reaction of the aliphatic hydroxyl group to ring-open the cyclic alpha-hydroxyacid dimer, lactone or cyclic carbonate, thereby providing monomers which endow their corresponding polymers with desirable physicochemical and degradation properties, vide infra.

The polymers described herein may be synthesized by various conventional reactions known in the art.

For example, the hydroxyacid-phenolic monomer compounds can be reacted with aliphatic or aromatic dicarboxylic acids in a carbodiimide-mediated direct polyesterification using DPTS as a catalyst to form aliphatic or aromatic polyarylates. Examples of dicarboxylic acids suitable for the polymerization to form polyarylates have the structure of Formula (XVII):

$$\text{HO—C(=O)—R}^{14}\text{—C(=O)—OH,} \quad \text{(XVII)}$$

in which, for the aliphatic polyarylates, $R^{14}$ is selected from saturated and unsaturated, substituted and unsubstituted alkyl or alkylaryl groups containing up to 18 carbon atoms, and preferably from 2 to 12 carbon atoms. For the aromatic polyarylates, $R^{14}$ is selected from aryl groups containing up to 18 carbon atoms and preferably from 6 to 12 carbon atoms. In some embodiments, $R^{14}$ is defined as above for $R^8$.

$R^{14}$ is preferably selected so that the dicarboxylic acids employed as starting materials are either important naturally-occurring metabolites or highly biocompatible compounds. Examples of preferred aliphatic dicarboxylic acid starting materials are described elsewherein herein.

The polyarylates can also be prepared by the method disclosed by Higashi et al., J. Polym. Sci.: Polym. Chem. Ed., 21, 3233-9 (1983) using arylsulfonyl chloride as the condensing agent, by the process of Higashi et al., J. Polym. Sci.: Polym. Chem. Ed., 21, 3241-7 (1983) using diphenyl chlorophosphate as the condensing agent, by the process of Higashi et al., J. Polym. Sci.: Polym. Chem. Ed., 24, 97-102 (1986) using thionyl chloride with pyridine as the condensing agent, or by the process of Elias, et al., Makromol. Chem., 182, 681-6 (1981) using thionyl chloride with triethylamine. A preferred polyesterification procedure is the method disclosed by Moore et al., Macromol., 23, 65-70 (1990) utilizing carbodiimide coupling reagents as the condensing agents with the specially designed catalyst DPTS.

A particularly preferred polyesterification technique modifies the method of Moore to utilize an excess of the carbodiimide coupling reagent. This technique tends to produce aliphatic polyarylates having molecular weights greater than those obtained by Moore. Essentially any carbodiimide commonly used as a coupling reagent in peptide chemistry can be used as a condensing agent in the preferred polyesterification process. Such carbodiimides are well-known and disclosed in Bodanszky, Practice of Peptide Synthesis (Springer-Verlag, New York, 1984) and include dicyclohexylcarbodiimide, diisopropylcarbodiimide, 1-(3-dimethylamino-propyl)-3-ethyl carbodiimide hydrochloride, N-cyclohexyl-N'-(2'-morpholinoethyl)-carbodiimide-metho-p-toluene sulfonate, N-benzyl-N'-3'-dimethyl-aminopropyl-carbodiimide hydrochloride, 1-ethyl-3-(3-dimethylaminopropyl)-carbodiimide meth-iodide, N-ethylcarbodiimide hydrochloride, and the like. The preferred carbodiimides are dicyclohexyl carbodiimide and diisopropylcarbodiimide.

An esterification reaction mixture can generally be formed by contacting exactly equimolar quantities of the hydroxyacid-phenolic compound and the dicarboxylic acid in a solvent. Suitable solvents include methylene chloride, tetrahydrofuran, dimethylformamide, chloroform, carbon tetrachloride and N-methyl pyrrolidinone. It is not necessary to bring all reagents into complete solution prior to initiating the polyesterification reaction, although the polymerization of slightly soluble monomers such as desaminotyrosyltyrosine ethyl ester and succinic acid will typically yield higher molecular weight polymers when the amount of solvent is increased. The reaction mixture can also be heated gently to aid in the partial dissolution of the reactants.

The polyarylates can be worked up and isolated by known methods commonly employed in the field of synthetic polymers to produce a variety of useful articles with valuable physical and chemical properties, all derived from tissue compatible monomers. The useful articles can be shaped by conventional polymer-forming techniques such as extrusion, compression molding, injection molding, and the like. Molded articles prepared from the polyarylates are useful, inter alia, as degradable biomaterials for medical implant applications. Such applications include the use of the molded articles as vascular grafts and stents, bone plates, sutures, implantable sensors, barriers for surgical adhesion prevention, implantable drug delivery devices and other therapeutic aids and articles which decompose harmlessly within a known period of time.

In some embodiments the polymers described herein contain phosphorus. The versatility of these polymers may come from the versatility of the phosphorus atom, which is known for a multiplicity of reactions. Its bonding may involve the 3p orbitals or various 3s-3p hybrids; spd hybrids are also possible because of the accessible of orbitals. Thus, the physico-chemical properties of the poly(phosphoesters) may be readily changed by varying either the R or R' group. The biodegradability of the polymer is due primarily to the physiologically labile phosphoester bond in the backbone of the polymer. By manipulating the backbone or the sidechain, a wide range of biodegradation rates are attainable.

As those skilled in the art would appreciate, when a monomer has an unsymmetrical structure having two equally or similarly reactive functional groups for polymerization, the polymers formed would largely contain the monomeric units in random orders.

Poly(phosphonates) may be prepared by a similar condensation between appropriately substituted dichlorides and diols.

Poly(phosphites) may be prepared from glycols in a two-step condensation reaction. A 20% molar excess of a dimethylphosphite is preferably used to react with the glycol, followed by the removal of the methoxyphosphonyl end groups in the oligomers by high temperature. An advantage of melt polycondensation is that it avoids the use of solvents and large amounts of other additives, thus making purification more straightforward. It may also provide polymers of reasonably high molecular weight. Polymerization may also be carried out in solution. A chlorinated organic solvent may be used, such as chloroform, dichloromethane, or dichloroethane. To achieve high molecular weights, the solution polymerization is preferably run in the presence of equimolar amounts of the reactants and, more preferably, a stoichiometric amount of an acid acceptor or a Lewis acid-type catalyst. Useful acid acceptors include tertiary amines such as pyridine or triethylamine. Examples of useful Lewis acid-type catalysts include magnesium chloride and calcium chloride. The product may be isolated from the solution by precipitation in a non-solvent and purified to remove the hydrochloride salt by conventional techniques known to those of ordinary skill in the art, such as by washing with an aqueous acidic solution, e.g., dilute HCl.

Halogenated phenolic monomers may also be polymerized to form polyiminocarbonates utilizing cyanogen bromide. Polyiminocarbonates are structurally related to polycarbonates. The polyiminocarbonates have imino groups in the places typically occupied by carbonyl oxygen in the polycarbonates. Thus, the polyiminocarbonates have linkages according to the formula:

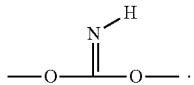

Inclusion of iminocarbonate linkages may impart a significant degree of hydrolytic instability to the polymer. The polyiminocarbonates have desirable mechanical properties akin to those of the corresponding polycarbonates.

Starting materials described herein are available commercially, are known, or may be prepared by methods known in the art. Additionally, starting materials not described herein are available commercially, are known, or may be prepared by methods known in the art.

Starting materials may have the appropriate substituents to ultimately give desired products with the corresponding substituents. Alternatively, substituents may be added at any point of synthesis to ultimately give desired products with the corresponding substituents.

The synthetic schemes illustrated herein show methods that may be used to prepare the compounds of preferred embodiments. One skilled in the art will appreciate that a number of different synthetic reaction schemes may be used to synthesize the compounds of preferred embodiments. Further, one skilled in the art will understand that a number of different solvents, coupling agents and reaction conditions may be used in the synthetic reactions to yield comparable results.

One skilled in the art will appreciate variations in the sequence and, further, will recognize variations in the appropriate reaction conditions from the analogous reactions shown or otherwise known which may be appropriately used in the processes above to make the compounds of preferred embodiments.

In the processes described herein for the preparation of the compounds of preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis". Wiley (New York), 1999.

The products of the reactions described herein can be isolated by conventional means such as precipitation, extraction, distillation, chromatography, and the like.

The salts of the compounds described herein can be prepared by reacting the base or acid as appropriate with a stoichiometric equivalent of the compound.

In some embodiments, the polymer comprises poly(ether carbonate) with a tyrosol-bioactive moiety. A hydroxyacid-tyrosol compound can be combined with the PEG in methylene chloride and phosgene can be added as a solution in toluene. The reaction would be completed in around 9 minutes. In some embodiments, this reaction is carried out for from 1-60 minutes. In an embodiment, the polymer comprises poly(hydroxyacid-tyrosol carbonate) pendant bioactive moiety groups.

In another aspect the present invention provides a medical device that comprises a polymer and/or polymer composition as described herein. For example, an embodiment provides a stent that comprises a polymer composition as described herein. Another embodiment provides a method of treating a body lumen, comprising deploying the stent within the body lumen. These and other embodiments are described in greater detail below.

Definitions

The term "biodegradable," as used herein, refers to a property of polymer whose molecular weight goes down because of hydrolysis or enzymatic reactions under physiological conditions such that the polymer is transformed into lower molecular weight oligomers in a period not to exceed four (4) years.

The term "oligomer," as used herein, refers to a hydrolyzed product of a polymer, whose molecular weight is less than 10% of the original polymer.

The terms "alkyl", "alkylene" and similar terms have the usual meaning known to those skilled in the art and thus may be used to refer to straight or branched hydrocarbon chain fully saturated (no double or triple bonds) hydrocarbon group. Terminal alkyl groups, e.g., of the general formula —$C_nH_{2n+1}$, may be referred to herein as "alkyl" groups, whereas linking alkyl groups, e.g., of the general formula —$(CH_2)_n$—, may be referred to herein as "alkylene" groups. The alkyl group may have 1 to 50 carbon atoms (whenever it appears herein, a numerical range such as "1 to 50" refers to each integer in the given range; e.g., "1 to 50 carbon atoms" means that the alkyl group may consist of 1 carbon atom, 2 carbon atoms, 3 carbon atoms, etc., up to and including 50 carbon atoms, although the present definition also covers the occurrence of the term "alkyl" where no numerical range is designated). The alkyl group may also be a medium size alkyl having 1 to 30 carbon atoms. The alkyl group could also be a "lower alkyl", which is defined as having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl and the like.

The alkyl group may be substituted or unsubstituted. When substituted, the substituent group(s) is(are) one or more group(s) individually and independently selected from alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. Wherever a substituent is described as being "optionally substituted" that substituent may be substituted with one of the above substituents.

An "alkylaryl" is an aryl group connected, as a substituent, via an alkylene group. The alkylene and aryl group of an aralkyl may be substituted or unsubstituted. Examples include but are not limited to benzyl, substituted benzyl, 2-phenylethyl, 3-phenylpropyl, and naphthylalkyl. In some cases, the alkylene group is a lower alkylene group containing 1 to 6 carbon atoms. An alkylaryl group may be substituted or unsubstituted.

As noted above, alkyl groups may link together other groups, and in that context may be referred to as alkylene groups. Alkylene groups are thus biradical tethering groups, forming bonds to connect molecular fragments via their terminal carbon atoms. Examples include but are not limited to methylene (—CH—), ethylene (—$CH_2CH_2$—), propylene (—$CH_2CH_2CH_2$—), and butylene (—$(CH_2)_4$—) groups. An alkylene group may be substituted or unsubstituted.

The terms "alkenyl", "alkenylene" and similar terms have the usual meaning known to those skilled in the art and thus may be used to refer to an alkyl or alkylene group that contains in the straight or branched hydrocarbon chain containing one or more double bonds. An alkenyl group may be unsubstituted or substituted. When substituted, the substituent(s) may be selected from the same groups disclosed above with regard to alkyl group substitution unless otherwise indicated.

An "amide" is a chemical moiety with formula —$(R)_n$—C(=O)NHR' or —$(R)_n$—NHC(=O)R', where R and R' are independently selected from the group consisting of alkyl, cycloalkyl, aryl, heteroaryl (bonded through a ring carbon) and heteroalicyclic (bonded through a ring carbon), and where n is 0 or 1. An amide may be an amino acid or a peptide molecule attached to a molecule of the present invention, thereby forming a prodrug. An "amide linkage" is an amide group (—C(=O)NH—) that links two chemical moieties to one another.

Any amine, hydroxy, or carboxyl side chain on the compounds disclosed herein can be esterified or amidified. The procedures and specific groups to be used to achieve this end are known to those of skill in the art and can readily be found in reference sources such as Greene and Wuts, Protective Groups in Organic Synthesis, 3rd Ed., John Wiley & Sons, New York, N.Y., 1999, which is incorporated by reference herein in its entirety.

As used herein, "aryl" refers to a carbocyclic (all carbon) ring or two or more fused rings (rings that share two adjacent carbon atoms) that have a fully delocalized pi-electron system. Examples of aryl groups include, but are not limited to, benzene, naphthalene and azulene. An aryl group may be substituted or unsubstituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (hetero-alicyclyl)alkyl, hydroxy, protected hydroxy, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy. O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. When substituted, substituents on an aryl group may form a non-aromatic ring fused to the aryl group, including a cycloalkyl, cycloalkenyl, cycloalkynyl, and heterocyclyl.

As used herein, "heteroalkyl" refers to an alkyl group where one or more carbon atoms has been replaced with a heteroatom, that is, an element other than carbon, including but not limited to, nitrogen, oxygen and sulfur.

The terms "heteroalkyl", "heteroalkylene," and similar terms have the usual meaning known to those skilled in the art and thus may be used to refer to an alkyl group or alkylene group as described herein in which one or more of the carbons atoms in the backbone of alkyl group or alkylene group has been replaced by a heteroatom such as nitrogen, sulfur and/or oxygen. Likewise, the term "heteroalkenylene" may be used to refer to an alkenyl or alkenylene group in which one or more of the carbons atoms in the backbone of alkyl group or alkylene group has been replaced by a heteroatom such as nitrogen, sulfur and/or oxygen.

As used herein. "heteroaryl" refers to an aryl group where one or more carbon atoms has been replaced with a heteroatom, that is, an element other than carbon, including but not limited to, nitrogen, oxygen and sulfur.

For convenience and conciseness, sometimes the terms "alkyl", "alkenyl", "alkynyl", "aryl", "heteroaryl", and "alkylaryl", or the like, may be used to refer to the corresponding linking groups when they serve to connect two moieties of a molecule, either monomeric or polymeric, which should be readily understood by those skilled in the art. That is, on such occasions, "alkyl" should be interpreted as "alkylene"; "alkenyl" should be interpreted as "alkenylene"; "aryl" should be interpreted as "arylene"; and so on.

A "heavy atom" is an atom that, when attached to a polymer, renders the polymer easier to detect by an imaging technique as compared to a polymer that does not contain the heavy atom. Since many polymers contain relatively low atomic number atoms such as hydrogen, carbon, nitrogen, oxygen, silicon and sulfur, in most cases heavy atoms have an atomic number of 17 or greater. Preferred heavy atoms have an atomic number of 35 or greater, and include bromine, iodine, bismuth, gold, platinum tantalum, tungsten, and barium.

A "hydrocarbon" is an organic compound consisting entirely of hydrogen and carbon. Examples of hydrocarbons include unsubstituted alkyl groups, unsubstituted aryl groups, and unsubstituted alkylaryl groups. Any substitution to an alkyl group, aryl group, or alkylaryl group in a hydrocarbon would only comprise carbon and/or hydrogen atoms.

As used herein, the terms "macromer", "macromeric" and similar terms have the usual meaning known to those skilled in the art and thus may be used to refer to oligomeric and polymeric materials that are functionalized with end groups that are selected so that the macromers can be copolymerized with other macromers or monomers. A wide variety of macromers and methods for making them are known to those skilled in the art. Examples of suitable macromers include hydroxy endcapped polylactic acid macromers, hydroxy endcapped polyglycolic acid macromers, hydroxy endcapped poly(lactic acid-co-glycolic acid) macromers, hydroxy endcapped polycaprolactone macromers, poly (alkylene diol) macromers, hydroxy endcapped poly(alkylene oxide) macromers and hydroxy endcapped polydioxanone macromers.

As used herein, the terms "polymer", "polymeric" and similar terms have the usual meaning known to those skilled in the art and thus may be used to refer to homopolymers, copolymers (e.g., random copolymer, alternating copolymer, block copolymer, graft copolymer) and mixtures thereof. The repeating structural units of polymers may also be referred to herein as recurring units.

As used herein, the term "molecular weight" has the usual meaning known to those skilled in the art and thus reference herein to a polymer having a particular molecular weight will be understood as a reference to a polymer molecular weight in units of Daltons. Various techniques known to those skilled in the art, such as end group analysis (e.g., by $^1$H NMR) and high pressure size exclusion chromatography (HPSEC, also known as gel permeation chromatography, "GPC"), may be used to determine polymer molecular weights. In some cases the molecular weights of polymers are further described herein using the terms "number average" molecular weight (Mn) and/or "weight average" molecular weight (Mw), both of which terms are likewise expressed in units of Daltons and have the usual meaning known to those skilled in the art.

Unless otherwise indicated, when a substituent is deemed to be "optionally substituted," it is meant that the substitutent is a group that may be substituted with one or more group(s) individually and independently selected from alkyl, alkenyl, alkylyl, cycloalkyl, aryl, heteroaryl, heteroalicyclic, hydroxyl, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art and may be found in references such as Greene and Wuts, above.

The terms "radiopaque", "radio-opaque", "radiopacity", "radio-opacity", "radiopacifying" and similar terms have the usual meaning known to those skilled in the art and thus may be used to refer to polymer compositions that have been rendered easier to detect using medical imaging techniques (e.g., by X-ray and/or during fluoroscopy) being the incorporation of heavy atoms into the polymer composition. Such incorporation may be by mixing, e.g., by mixing an effective amount of a radiopacifying additive such as barium salt or complex, and/or by attachment of effective amounts of heavy atoms to one or more of the polymers in the polymer composition.

In certain configurations, polymer compositions may be inherently radiopaque. The term "inherently radiopaque" is used herein to refer to a polymer to which a sufficient number of heavy atoms are attached by covalent or ionic bonds to render the polymer radiopaque. This meaning is consistent with the understanding of those skilled in the art, see, e.g., U.S. Patent Publication No. 2006/0024266, which is hereby incorporated by reference for all purposes, including for the particular purpose of describing radiopaque polymeric materials.

Whenever a group is described as being "optionally substituted" that group may be unsubstituted or substituted with one or more of the indicated substituents. Likewise, when a group is described as being "unsubstituted or substituted" if substituted, the substituent may be selected from one or more the indicated substituents.

Unless otherwise indicated, when a substituent is deemed to be "optionally substituted," or "substituted" it is meant that the substituent is a group that may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, cyano, halogen, carbonyl, thiocarbonyl, O-carbamyl, N-carbamyl, O-thiocarbamyl, N-thiocarbamyl, C-amido, N-amido. S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. Similarly, the term "optionally ring-halogenated" may be used to refer to a group that optionally contains one or more (e.g., one, two, three or four) halogen substituents on the aryl and/or heteroaryl ring. The protecting groups that may form the protective derivatives of the above substituents are known to those of skill in the art and may be found in references such as Greene and Wuts, Protective Groups in Organic Synthesis, 3$^{rd}$ Ed., John Wiley & Sons, New York, N.Y., 1999, which is hereby incorporated by reference in its entirety.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. Thus, the alpha-hydroxyacids employed as subunits in the monomers and their resulting polymers can be chiral, vide infra. For example, the lactate-derived monomers and polymers can be derived from L-lactic acid, D-lactic acid or the racemic D,L-lactic acid. Further, specific blocks of L-lactate, D-lactate and/or D,L-lactate can be incorporated in any order. In addition it is understood that, in any compound having one or more double bond(s) generating geometrical isomers that can be defined as E or Z each double bond may independently be E or Z a mixture thereof. Likewise, all tautomeric forms are also intended to be included.

The following abbreviations are used to identify various iodinated compounds. TE stands for tyrosine ethyl ester, DAT stands for desaminotyrosine and DTE for desaminotyrosyl tyrosine ethyl ester. PTE stands for hydroxy-phenoxy-1-oxoethyl tyrosine ethyl ester. Ty stands for tyrosol. The polymer obtained by phosgenation of DTE is denoted as poly(DTE carbonate). An "I" before the abbreviation shows mono-iodination (e.g. ITE stands for mono-iodinated TE) and an I$_2$ before the abbreviation shows di-iodination (e.g. I$_2$DAT stands for di-iodinated DAT). In DTE, if the "I" is before D, it means the iodine is on DAT and if "I" is after D, it means the iodine is on the tyrosine ring (e.g. DI$_2$TE stands for DTE with 2 iodine atoms on the tyrosine ring). The following diagram illustrates this nomenclature further.

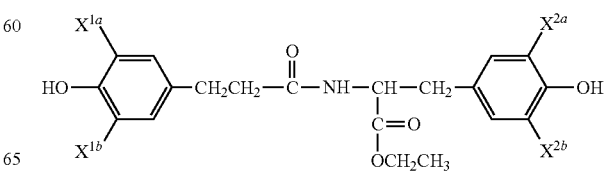

General Structure of Iodinated DTE Monomer

IDTE: $X^{1a}$=I, $X^{1b}$=H, $X^{2a}$=H, $X^{2b}$=H.
$I_2$DTE: $X^{1a}$=I, $X^{1b}$=I, $X^{2a}$=H, $X^{2b}$=H
$DI_2$TE: $X^{1a}$=H, $X^{1b}$==H, $X^{2a}$=I, $X^{2b}$=I
IDITE: $X^{1a}$=I, $X^{1b}$=H, $X^{2a}$=I, $X^{2b}$=H

For PTE, PTH, IPTE, $I_2$PTE, $PI_2$TE, etc., the DAT $CH_2CH_2$ is replaced with $OCH_2$.

As used herein, the abbreviations for any protective groups, amino acids and other compounds are, unless indicated otherwise, in accord with their common usage, recognized abbreviations, or the IUPAC-IUP Commission on Biochemical Nomenclature (See, Biochem. 11:942-944 (1972)).

The term "halogen atom," as used herein, means any one of the radio-stable atoms of column 7 of the Periodic Table of the Elements, e.g., fluorine, chlorine, bromine, or iodine, with bromine and iodine being preferred.

The term "ester" refers to a chemical moiety with formula —$(R)_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1. An "ester linkage" is an ester group that links two chemical moieties to one another.

The terms "purified," "substantially purified," and "isolated" as used herein refer to compounds disclosed herein being substantially free of other, dissimilar compounds with which the compounds of the invention are normally associated in their natural state, so that the compounds of the invention comprise at least 0.5%, 1%, 5%, 10%, or 20%, and most preferably at least 50% or 75% of the mass, by weight, of a given sample.

It is understood that the polymers described herein may be used in accordance with preferred aspects of the invention as a homogeneous polymer, as a copolymer, and/or as a polymer blend.

Although the inventors do not wish to be bound by or to any particular theory of operation, the inventors believe that the beneficial combination of properties associated with the medical devices of the present invention are attributable, at least in part, to certain characteristics of the polymers disclosed herein, from which the devices are made.

The tyrosol-lactate diol macromers, as described below, have the unique attribute of possessing the crystallizable poly-lactate units on only one side of the macromer. This derives from the surprising observation that when ring opening of a lactide (or lactone or cyclic carbonate) is initiated with tyrosol, only the aliphatic OH group participates in the ring opening reactions, thereby leaving the phenolic OH free. One embodiment has the following structure:

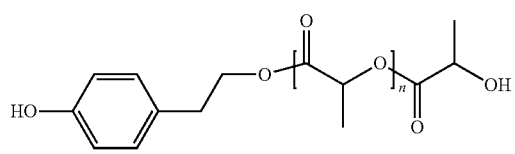

For a conventional diol macromer prepared from a lactide and an α,ω-diol, the initiating diol reacts with the lactide equally on both ends of the diol. One embodiment using propane diol has the following structure:

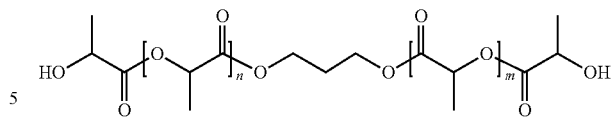

In this standard diol case, the diol initiator is generally embedded in the center of the resulting macromer entity and acts as a significant disruptor to molecular chain alignment. As a consequence, the polymer derived from these macromer units will have a lower melt transition, heat of fusion, and glass transition temperature than would be expected from non-disrupted polylactate chain segments.

Conversely, the tyrosol-polylactate units have no disruptor in the middle of the extended chain segments. This has the unexpected influence of providing a final polymer with a higher wet and dry glass transition temperature (Tg) and a crystalline phase with higher melt temperature and heat of fusion, thus a better crystalline phase. The higher wet Tg of biodegradable structural polymers is critically significant in that the wet Tg needs to be sufficiently above body temperature to maintain the required level of mechanical structural support. Because of their unique chain architecture, the tyrosol-polylactates provide a higher wet Tg. Obtaining the correct wet Tg and crystalline phase is not possible using the standard diol chemistry.

The bioresorbable, inherently radiopaque stents disclosed in accordance with preferred embodiments of the present invention may be used, for example, to temporarily treat a blood vessel as in traditional applications which generally include delivery through a catheter.

In some embodiments polymers prepared from sufficient amounts of the monomeric starting materials described herein and having at least one bromine- or iodine-substituted aromatic ring are radio-opaque, such as the polymers prepared from radiopaque diphenol compounds prepared according to the disclosure of U.S. Pat. No. 6,475,477, as well as the disclosure of U.S. Pat. No. 7,649,150, the disclosures of both of which are incorporated herein by reference. The iodinated and brominated hydroxyacid-phenolic monomers of the present invention can also be employed as radio-opacifying, biocompatible non-toxic additives for other polymeric biomaterials.

Bromine and iodine substituted aromatic monomers of the present invention can be prepared by well-known iodination and bromination techniques that can be readily employed by those of ordinary skill in the art in view of the guidance provided herein without undue experimentation. In some embodiments, the halogenated aromatic compounds from which the halogenated aromatic monomers of the present invention are prepared typically undergo ortho-directed halogenation. The term, "ortho-directed", is used herein to designate orientation of the halogen atom(s) relative to the phenoxy alcohol group.

Benzyl ester-containing homopolymers and copolymers may be converted to corresponding free carboxylic acid homopolymers and copolymers through the selective removal of the benzyl groups by the palladium catalyzed hydrogenolysis method disclosed by co-pending and commonly owned U.S. Pat. No. 6,120,491, the disclosure of which is incorporated herein by reference.

Tert-butyl ester-containing homopolymers and copolymers may be converted to corresponding free carboxylic acid homopolymers and copolymers through the selective removal of the tert-butyl groups by the acidolyis method disclosed by the above-referenced U.S. Pat. No. 7,649,150, also incorporated herein by reference.

After polymerization, appropriate work up of the polymers in accordance with preferred embodiments of the present invention may be achieved by any of a variety of known methods commonly employed in the field of synthetic polymers to produce a variety of useful articles with valuable physical and chemical properties, all derived from tissue compatible monomers. The useful articles can be shaped by conventional polymer-forming techniques such as extrusion, compression molding, injection molding, solvent casting, spin casting, wet spinning, combinations of two or more thereof, and the like. Shaped articles prepared from the polymers are useful, inter alia, as degradable biomaterials for medical implant applications. Such applications include the use of shaped articles as vascular grafts and stents.

Polymers according to the present invention also include polyethers, polyurethanes, poly(carbamates), poly(thiocarbonates), poly(carbonodithionates) and poly(thiocarbamates), which may be prepared from the hydroxyacid-phenolic compounds of the present invention in accordance with known methods.

Random or block copolymers of the polymers of the present invention with a poly(alkylene oxide) may be prepared according to the method disclosed in U.S. Pat. No. 5,658,995, the disclosure of which is also incorporated by reference. The poly(alkylene oxide) is preferably a poly(ethylene glycol) block/unit typically having a molecular weight of less than about 10,000 per unit. More typically, the poly(ethylene glycol) block/unit has a molecular weight less than about 4000 per unit. The molecular weight is preferably between about 1000 and about 2000 per unit.

The molar fraction of poly(ethylene glycol) units in block copolymers may range from greater than zero to less than 1, and is typically greater than zero up to about 0.5, inclusive. More preferably, the molar fraction is less than about 0.25 and yet more preferably, less than about 0.1. In a more preferred variations, the molar fraction may vary from greater than about 0.001 to about 0.08, and most preferably, between about 0.025 and about 0.035.

Unless otherwise indicated, the molar fractions reported herein are based on the total molar amount of poly(alkylene glycol) and non-glycol units in the polymers After polymerization, appropriate work up of the polymers in accordance with preferred embodiments of the present invention may be achieved by any of a variety of known methods commonly employed in the field of synthetic polymers to produce a variety of useful articles with valuable physical and chemical properties, all derived from tissue compatible monomers. The useful articles can be shaped by conventional polymer thermo-forming techniques such as extrusion and injection molding when the degradation temperature of the polymer is above the glass transition or crystalline melt temperature, or conventional non-thermal techniques can be used, such as compression molding, injection molding, solvent casting, spin casting, wet spinning. Combinations of two or more methods can be used. Shaped articles prepared from the polymers are useful, inter alia, as degradable biomaterials for medical implant applications.

Medical Uses

Various embodiments of the polymer compositions described herein, preferably derived from tissue compatible monomers, may be used to produce a variety of useful articles with valuable physical and chemical properties. The useful articles can be shaped by conventional polymer thermo-forming techniques such as extrusion and injection molding when the degradation temperature of the polymer is above the glass transition or crystalline melt temperature(s), or conventional non-thermal techniques can be used, such as compression molding, injection molding, solvent casting, spin casting, wet spinning. Combinations of two or more methods can be used. Shaped articles prepared from the polymers are useful, inter alia, as biocompatible, biodegradable and/or bioresorbable biomaterials for medical implant applications.

In one embodiment, the medical device is a stent. It is contemplated that a stent may comprise many different types of forms. For instance, the stent may be an expandable stent. In another embodiment, the stent may be configured to have the form of a sheet stent, a braided stent, a self-expanding stent, a woven stent, a deformable stent, or a slide-and-lock stent. Stent fabrication processes may further include two-dimensional methods of fabrication such as cutting extruded sheets of polymer, via laser cutting, etching, mechanical cutting, or other methods, and assembling the resulting cut portions into stents, or similar methods of three-dimensional fabrication of devices from solid forms.

In certain other embodiments, the polymers are formed into coatings on the surface of an implantable device, particularly a stent, made either of a polymer as described herein or another material, such as metal. Such coatings may be formed on stents via techniques such as dipping, spray coating, combinations thereof, and the like. Further, stents may be comprised of at least one fiber material, curable material, laminated material and/or woven material. The medical device may also be a stent graft or a device used in embolotherapy.

The highly beneficial combination of properties associated with preferred embodiments of the polymers described herein means these polymers are well-suited for use in producing a variety of resorbable medical devices besides stents, especially implantable medical devices that are preferably radiopaque, biocompatible, and have various times of bioresorption. For example the polymers are suitable for use in resorbable implantable devices with and without therapeutic agents, device components and/or coatings with and without therapeutic agents for use in other medical systems, for instance, the musculoskeletal or orthopedic system (e.g., tendons, ligaments, bone, cartilage skeletal, smooth muscles); the nervous system (e.g., spinal cord, brain, eyes, inner ear); the respiratory system (e.g., nasal cavity and sinuses, trachea, larynx, lungs); the reproductive system (e.g., male or female reproductive); the urinary system (e.g., kidneys, bladder, urethra, ureter); the digestive system (e.g., oral cavity, teeth, salivary glands, pharynx, esophagus, stomach, small intestine, colon), exocrine functions (biliary tract, gall bladder, liver, appendix, recto-anal canal); the endocrine system (e.g., pancreas/islets, pituitary, parathyroid, thyroid, adrenal and pineal body), the hematopoietic system (e.g., blood and bone marrow, lymph nodes, spleen, thymus, lymphatic vessels); and, the integumentary system (e.g., skin, hair, nails, sweat glands, sebaceous glands).

The polymers described herein can thus be used to fabricate wound closure devices, hernia repair meshes, gastric lap bands, drug delivery implants, envelopes for the implantation of cardiac devices, devices for other cardiovascular applications, non-cardiovascular stents such as biliary stents, esophageal stents, vaginal stents, lung-trachea/bronchus stents, and the like.

In addition, the resorbable polymers are suitable for use in producing implantable, radiopaque discs, plugs, and other devices used to track regions of tissue removal, for example, in the removal of cancerous tissue and organ removal, as well as, staples and clips suitable for use in wound closure, attaching tissue to bone and/or cartilage, stopping bleeding (homeostasis), tubal ligation, surgical adhesion prevention, and the like. Applicants have also recognized that preferred embodiments of the polymers described herein are well-suited for use in producing a variety of coatings for medical devices, especially implantable medical devices.

Further, in some preferred embodiments, the present polymers may be advantageously used in making various resorbable orthopedic devices including, for example, radiopaque biodegradable screws (interference screws), radiopaque biodegradable suture anchors, and the like for use in applications including the correction, prevention, reconstruction, and repair of the anterior cruciate ligament (ACL), the rotator cuff/rotator cup, and other skeletal deformities.

Other devices that can be advantageously formed from preferred embodiments of the polymers described herein, include devices for use in tissue engineering. Examples of suitable resorbable devices include tissue engineering scaffolds and grafts (such as vascular grafts, grafts or implants used in nerve regeneration). The resorbable polymers may also be used to form a variety of devices effective for use in closing internal wounds. For example biodegradable resorbable sutures, clips, staples, barbed or mesh sutures, implantable organ supports, and the like, for use in various surgery, cosmetic applications, and cardiac wound closures can be formed.

Various devices useful in dental applications may advantageously be formed according to embodiments of the described herein. For example devices for guided tissue regeneration, alveolar ridge replacement for denture wearers, and devices for the regeneration of maxilla-facial bones may benefit from being radiopaque so that the surgeon or dentist can ascertain the placement and continuous function of such implants by simple X-ray imaging.

Preferred embodiments of the polymers described herein are also useful in the production of bioresorbable, inherently radiopaque polymeric embolotherapy products for the temporary and therapeutic restriction or blocking of blood supply to treat tumors and vascular malformations, e.g., uterine fibroids, tumors (i.e., chemoembolization), hemorrhage (e.g., during trauma with bleeding) and arteriovenous malformations, fistulas and aneurysms delivered by means of catheter or syringe. Details of embolotherapy products and methods of fabrication in which the polymers described herein may be employed are disclosed in U.S. Patent Publication No. 20050106119 A1, the disclosure of which is incorporated by reference, and particularly for the purpose of describing such products and methods. Embolotherapy treatment methods are by their very nature local rather than systemic and the products are preferably fabricated from the radio-opaque polymers described herein, to permit fluoroscopic monitoring of delivery and treatment.

The polymers described herein are further useful in the production of a wide variety of therapeutic agent delivery devices. Such devices may be adapted for use with a variety of therapeutics including, for example, pharmaceuticals (i.e., drugs) and/or biological agents as previously defined and including biomolecules, genetic material, and processed biologic materials, and the like. Any number of transport systems capable of delivering therapeutics to the body can be made, including devices for therapeutics delivery in the treatment of cancer, intravascular problems, dental problems, obesity, infection, and the like.

A medical device that comprises a polymeric material may include one or more additional components, e.g., a plasticizer, a filler, a crystallization nucleating agent, a preservative, a stabilizer, a photoactivation agent, etc., depending on the intended application. For example, in an embodiment, a medical device comprises an effective amount of at least one therapeutic agent and/or a magnetic resonance enhancing agent. Non-limiting examples of preferred therapeutic agents include a chemotherapeutic agent, a non-steroidal anti-inflammatory, a steroidal anti-inflammatory, and a wound healing agent. Therapeutic agents may be co-administered with the polymeric material. In a preferred embodiment, at least a portion of the therapeutic agent is contained within the polymeric material. In another embodiment, at least a portion of the therapeutic agent is contained within a coating on the surface of the medical device.

Non-limiting examples of preferred chemotherapeutic agents include taxanes, tax-inines, taxols, paclitaxel, dioxorubicin, cis-platin, adriamycin and bleomycin. Non-limiting examples of preferred non-steroidal anti-inflammatory compounds include aspirin, dexa-methasone, ibuprofen, naproxen, and Cox-2 inhibitors (e.g., Rofexcoxib, Celecoxib and Valdecoxib). Non-limiting examples of preferred steroidal anti-inflammatory compounds include dexamethasone, beclomethasone, hydrocortisone, and prednisone. Mixtures comprising one or more therapeutic agents may be used. Non-limiting examples of preferred magnetic resonance enhancing agents include gadolinium salts such as gadolinium carbonate, gadolinium oxide, gadolinium chloride, and mixtures thereof.

The amounts of additional components present in the medical device are preferably selected to be effective for the intended application. For example, a therapeutic agent is preferably present in the medical device in an amount that is effective to achieve the desired therapeutic effect in the patient to whom the medical device is administered or implanted. Such amounts may be determined by routine experimentation. In certain embodiments, the desired therapeutic effect is a biological response. In an embodiment, the therapeutic agent in the medical device is selected to promote at least one biological response, preferably a biological response selected from the group consisting of thrombosis, cell attachment, cell proliferation, attraction of inflammatory cells, deposition of matrix proteins, inhibition of thrombosis, inhibition of cell attachment, inhibition of cell proliferation, inhibition of inflammatory cells, and inhibition of deposition of matrix proteins. The amount of magnetic resonance enhancing agent in a medical devices is preferably an amount that is effective to facilitate radiologic imaging, and may be determined by routine experimentation.

The term "pharmaceutical agent", as used herein, encompasses a substance intended for mitigation, treatment, or prevention of disease that stimulates a specific physiologic (metabolic) response. The term "biological agent", as used herein, encompasses any substance that possesses structural and/or functional activity in a biological system, including without limitation, organ, tissue or cell based derivatives, cells, viruses, vectors, nucleic acids (animal, plant, microbial, and viral) that are natural and recombinant and synthetic in origin and of any sequence and size, antibodies, polynucleotides, oligonucleotides, cDNA's, oncogenes, proteins, peptides, amino acids, lipoproteins, glycoproteins, lipids, carbohydrates, polysaccharides, lipids, liposomes, or other cellular components or organelles for instance receptors and ligands. Further the term "biological agent", as used herein, includes virus, serum, toxin, antitoxin, vaccine, blood, blood component or derivative, allergenic product, or analogous product, or arsphenamine or its derivatives (or any trivalent organic arsenic compound) applicable to the prevention, treatment, or cure of diseases or injuries of man (per Section 351(a) of the Public Health Service Act (42 U.S.C. 262(a)). Further the term "biological agent" may include 1) "biomolecule", as used herein, encompassing a biologically active peptide, protein, carbohydrate, vitamin, lipid, or nucleic acid produced by and purified from naturally occurring or recombinant organisms, antibodies, tissues or cell lines or synthetic analogs of such molecules; 2) "genetic material" as used herein, encompassing nucleic acid (either deoxyribonucleic acid (DNA) or ribonucleic acid (RNA), genetic element, gene, factor, allele, operon, structural gene, regulator gene, operator gene, gene complement, genome, genetic code, codon, anticodon, messenger RNA (mRNA), transfer RNA (tRNA), ribosomal extrachromosomal genetic element, plasmagene, plasmid, transposon, gene mutation, gene sequence, exon, intron, and, 3) "processed biologics", as used herein, such as cells, tissues or organs that have undergone manipulation. The thera-peutic agent may also include vitamin or mineral substances or other natural elements.

For devices placed in the vascular system, e.g., a stent, the amount of the therapeutic agent is preferably sufficient to inhibit restenosis or thrombosis or to affect some other state of the stented tissue, for instance, heal a vulnerable plaque, and/or prevent rupture or stimulate endothelialization. The agent(s) may be selected from the group consisting of antiproliferative agents, anti-inflammatory, anti-matrix metalloproteinase, and lipid lowering, cholesterol modifying, anti-thrombotic and antiplatelet agents, in accordance with preferred embodiments of the present invention. In some preferred embodiments of the stent, the therapeutic agent is contained within the stent as the agent is blended with the polymer or admixed by other means known to those skilled in the art. In other preferred embodiments of the stent, the therapeutic agent is delivered from a polymer coating on the stent surface. In another preferred variation the therapeutic agent is delivered by means of no polymer coating. In other preferred embodiments of the stent, the therapeutic agent is delivered from at least one region or one surface of the stent. The therapeutic may be chemically bonded to the polymer or carrier used for delivery of the therapeutic of at least one portion of the stent and/or the therapeutic may be chemically bonded to the polymer that comprises at least one portion of the stent body. In one preferred embodiment, more than one therapeutic agent may be delivered.

In certain embodiments, any of the aforementioned devices described herein can be adapted for use as a therapeutic delivery device (in addition to any other functionality thereof). Controlled therapeutic delivery systems may be prepared, in which a therapeutic agent, such as a biologically or pharmaceutically active and/or passive agent, is physically embedded or dispersed within a polymeric matrix or physically admixed with a polymer described herein. Controlled therapeutic agent delivery systems may also be prepared by direct application of the therapeutic agent to the surface of an implantable medical device such as a bioresorbable stent device (comprised of at least one of the polymers described herein) without the use of these polymers as a coating, or by use of other polymers or substances for the coating.

Therapeutic agent delivery compounds may also be formed by physically blending the therapeutic agent to be delivered with the polymers described herein using conventional techniques well-known to those of ordinary skill in the art. For this therapeutic agent delivery embodiment, it is not essential that the polymer have pendent groups for covalent attachment of the therapeutic agent.

The polymer compositions described herein containing therapeutic agents, regardless of whether they are in the form of polymer conjugates or physical admixtures of polymer and therapeutic agent, are suitable for applications where localized delivery is desired, as well as in situations where a systemic delivery is desired. The polymer conjugates and physical admixtures may be implanted in the body of a patient in need thereof, by procedures that are essentially conventional and well-known to those of ordinary skill in the art.

The polyarylates can also be formed into drug delivery implants that degrade to release pharmacologically or biologically active agents within a predictable controlled release time. Such controlled drug delivery systems can be prepared by incorporating the active agents into the polymer chains as pendant side chains or by cross linking the pendant side chains to form a polymeric matrix into which the active agents are physically embedded or dispersed. Controlled drug delivery system implants can also be formed by physically admixing the polyarylates with a biologically or pharmacologically active agent. The foregoing procedures are essentially conventional and well-known to those of ordinary skill in the art.

For controlled drug delivery systems in which a biologically or pharmacologically active agent is physically embedded or dispersed into a polymeric matrix or physically admixed with a polyarylate, suitable biologically or pharmacologically active agents include in principle any active agent that has to be repeatedly administered over prolonged periods of time.

An advantage of using the radiopaque, bioresorbable polymers described herein in therapeutic agent delivery applications is the ease of monitoring release of a therapeutic agent and the presence of the implantable therapeutic delivery system. Because the radiopacity of the polymeric matrix is due to covalently attached halogen substituents, the level of radiopacity is directly related to the residual amount of the degrading therapeutic agent delivery matrix still present at the implant site at any given time after implantation. In preferred embodiments the rate of therapeutic release from the degrading therapeutic delivery system will be correlated with the rate of polymer resorption. In such preferred embodiments, the straight-forward, quantitative measurement of the residual degree of radio-opacity will provide the attending physician with a way to monitor the level of therapeutic release from the implanted therapeutic delivery system.

The following non-limiting examples set forth herein below illustrate certain aspects of the invention. All parts and percentages are by mole percent unless otherwise noted and all temperatures are in degrees Celsius unless otherwise indicated. All solvents were HPLC grade and all other reagents were of analytical grade and used as received, unless otherwise indicated.

EXAMPLES

All the reagents were purchased in pure form and were used as received. Solvents were of "HPLC" or "ACS reagent" grade.

Generally, the hydroxyacid-phenolic monomers were prepared by reaction of tyrosol with the cyclic dimers of alpha-hydroxyacids (e.g, glycolide, lactide, etc.), cyclic carbonates (e.g. trimethylene carbonate) or lactones. The number average molecular mass, $M_n$, of the resulting products is determined by the ratio of tyrosol to lactide in the reaction, and was confirmed by $^1$NMR spectroscopy. The hydroxy-acid-phenolic monomers in the pure form or as appropriate mixtures were polymerized to the corresponding polycarbonates using triphosgene. Similarly, polymerization of the hydroxyacid-phenolic monomers with diacids produced the corresponding polyesters. The resulting polymers were compression molded into films. The films were tested for mechanical properties and they generally showed high modulus, tensile strength, and elongation at break. Further details are provided below.

Example 1. Preparation of Tyrosyl Lactate282 (TyLactate282)

In a 2-L 3 necked flask equipped with a overhead stirrer, a nitrogen inlet adopter and a thermometer were placed 720.65 g (5.00 mol) of L-lactide, 690.35 g (5.00 mol) of tyrosol and 2.03 g (5.00 mmol) of Sn(II)octoate. The flask was maintained under a slight positive pressure of nitrogen and immersed in an oil bath. While stirring the contents of the flask the temperature of the oil bath was raised to 130° C. and maintained at that temperature for 3 h. The flask was then cooled to room temprature and the contents were dissolved in 3 liters of dichloromethane (DCM). The resulting solution was added to 6 liters of heptane with stirring. The supernatant was siphoned out and the precipiate was stirred with 3 1 L portions of hepane and dried in a vacuum oven at 35° C. for 24 h. HPLC showed approximately 6-8% unreacted tyro-sol, 35% of tyrosyl lactate, 36% of tyrosyl dilactate and higher oligomers. The results are confirmed by its $^1$H NMR spectrum. Using similar procedures Tyrosyl lactate210, Tyrosyl lactate426, Tyrosyl lactate1500, Tyrosyl lactate2500, Tyrosyl lactate4000, etc. were obtained by varying the ratio of tyrosol and lactide. As the ratio of lactide increased, the amount of residual tyrosol decreased and the product became more and more viscous. Tyrosyl lactate1500 and higher homologs were observed to be solids.

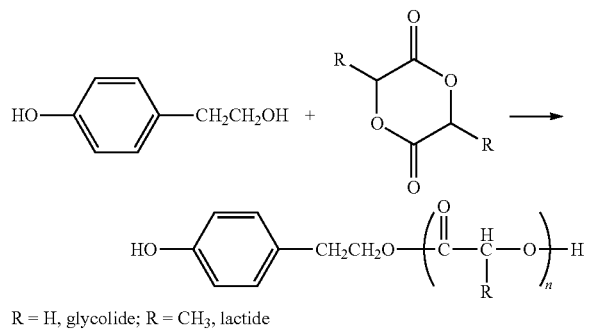

R = H, glycolide; R = CH$_3$, lactide

Example 2. Preparation of Tyrosyl Glycolate254 (TyGlycolate254)

Tyrosyl Glycolate254 was prepared using procedure similar to that used for Tyrosyl Lactate282 above. In a 1 L 3 necked flask equipped with an overhead stirrer, a nitrogen inlet adopter and a thermometer were placed 174.1 g (1.5 mol) of glycolide, 207.1 g (1.5 mol) of tyrosol and 0.6 g (1.5 mmol) of Sn(II)octoate. The flask was maintained under a slight positive pressure of nitrogen and immersed in an oil bath. While stirring the contents of the flask the temperature of the oil bath was raised to 140° C. and maintained at that temperature for 4 h. The flask was then cooled to room temprature and the contents were dissolved in 800 mL of dichloromethane (DCM). The resulting solution was added to 1.6 liters of heptane with stirring. The supernatant was siphoned out and the precipiate was stirred with 500 mL of hepane 3 times and then dried in a vacuum oven at 35° C. for 24 h. $^1$H NMR spectrum showed approximately 6% unreacted tyrosol. Using similar procedures Tyrosyl glycolates of molecular weight (Mn) 300 to 4000 were prepared.

Example 3. Iodination of Tyrosyl Lactate282

Iodination of Tyrosyl Lactate282 is carried out using known procedures. 200 mL of KICl$_2$ solution (2M) is added to 56.4 g (0.2 mol) of Tyrosyl Lactate282 in 250 mL of 95% ethanol and stirring the resulting solution for 1 h. It is then treated with 400 mL of water and the oil that separates is stirred with 100 mL of 2% sodium thiosulfate solution for 2 h. The brown solid obtained is dissolved in ethanol and treated with charcoal and filtered and evaporated to dryness to obtain diiodotyrosyl lactate282. The product is characterized by hplc and NMR.

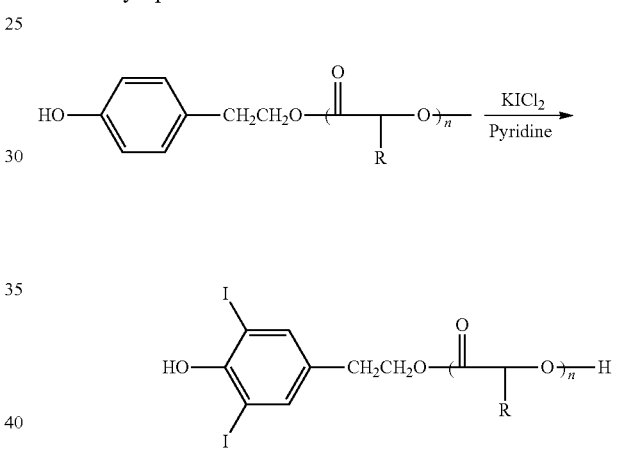

Example 4. Preparation of Tyrosyl Trimethylene Carbonate

Tyrosyl trimethylene carbonate is prepared using procedure similar to that used for Tyrosyl lactate282 above. In a 1 L 3 necked flask equipped with an overhead stirrer, and a nitrogen inlet adopter and a thermometer were placed 102.09 g (1.0 mol) of, trimethyelene carbonate 138.07 g (1.0 mol) of tyrosol and 0.4 g (1.0 mmol) of Sn(II)octoate. The flask was maintained under a slight positive pressure of nitrogen and immersed in a oil bath. While stirring the contents of the flask the temperature of the oil bath was raised to 130° C. and maintained at that temperature for 3 h. The flask was then cooled to room temprature and the contents were dissolved in 500 mL of dichloromethane (DCM). The resulting solution was added to 1.0 liters of heptane with stirring. The supernatant was siphoned out and the precipiate was stirred with 500 mL of hepane 3 times and then dried in a vacuum oven at 35° C. for 24 h. $^1$H NMR spectrum showed approximately 6% unreacted tyrosol. Using similar procedures Tyrosyl trimethylene carbonates of molecular weight (Mn) 300 to 4000 were prepared.

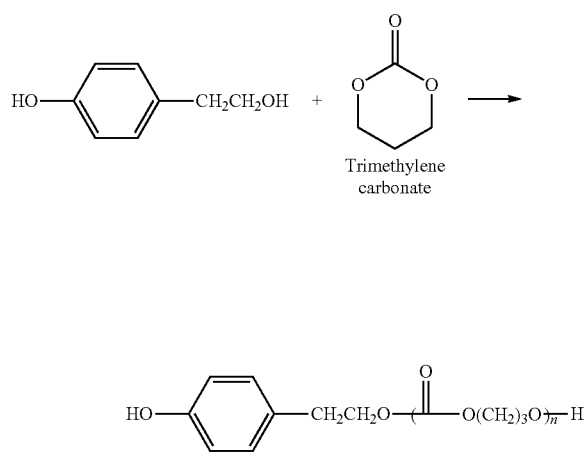

Example 5. Preparation of Tyrosyl Caprolactone

Tyrosyl caprolactone is prepared using procedure similar to that used for Tyrosyl trimethylene carbonate above. In a 1 L 3 necked flask equipped with an overhead stirrer, and a nitrogen inlet adopter and a thermometer are placed 114.14 g (1.0 mol) of, caprolactone 138.07 g (1.0 mol) of tyrosol and 0.4 g (1.0 mmol) of Sn(II)octoate. The flask is maintained under a slight positive pressure of nitrogen and immersed in a oil bath. While stirring the contents of the flask the temperature of the oil bath is raised to 130° C. and maintained at that temperature for 3 h. The flask is then cooled to room temperature and the contents were dissolved in 500 mL of dichloromethane (DCM). The resulting solution is added to 1.0 liters of heptane with stirring. The supernatant is siphoned out and the precipitate is stirred with 500 mL of hepane 3 times and then dried in a vacuum oven at 35° C. for 24 h. $^1$H NMR spectrum showed approximately 6% unreacted tyrosol. Using similar procedures Tyrosyl caprolactones of molecular weight (Mn) up to 4000 are prepared.

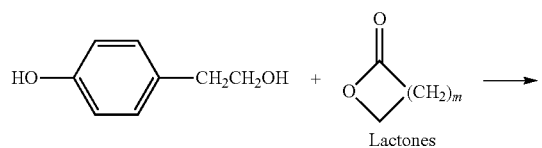

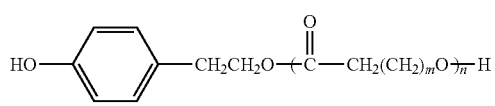

Example 6. Preparation of Poly(50% PrD-diI$_2$DAT-co-50% TyLactate426 Carbonate)

In a 5 L 4-necked round-bottomed flask equipped with a mechanical stirrer, a liquid addition device, and nitrogen inlet were placed 150 g (0.17 mol) of PrD-di I$_2$DAT, 150 g (0.35 mol) of TyLactate426, 155 g (1.96 mol) of pyridine, and 2.1 L of DCM and stirred for 15 min to get a clear solution. Triphosgene (54.3 g, 0.523 mol of phosgene) was dissolved in 150 mL of DCM and the solution was introduced into the reaction flask over 3 hours. After the addition was complete, the 500 mL of water was added to the reaction mixture and stirred for 5 min. After allowing the layers to separate, the top aqueous layer was removed and discarded. The washing was repeated with two additional 500 mL portions of DI water. The reaction mixture was then precipitated with 300 mL of isopropyl alcohol (IPA). The resulting gel was ground twice with 200 mL portions of IPA in 1 L laboratory blender. The product was isolated by vacuum filtration and dried in a vacuum oven at 80° C. The polymer had an absolute molecular weight of 221 Kda (PDI=1.86) and glass transition temperature (Tg) of 72° C. (wet Tg was 50° C. using DMA). $^1$H NMR spectrum of the polymer was in agreement with the structure. Compression molding at 190° C. gave a uniform transparent film which exhibited tensile modulus, tensile stress at yield (a), and elongation at break respectively of 249 ksi, 7.7 ksi and 333%. Using similar procedures, copolymers with 40%, and 30% TyLactate426 were also prepared by varying the ratio of PrD-di I$_2$DAT to TyLactate426. This polymer could be injection moldable at 190° C. and melt extrudable with minimal degradation.

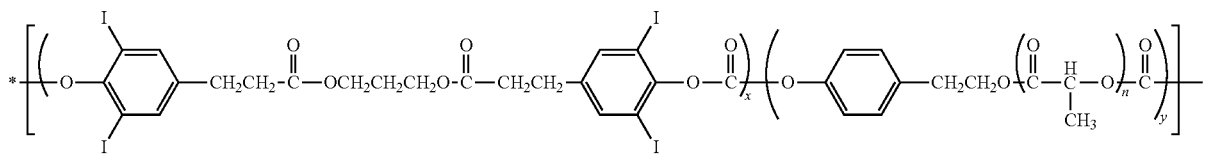

Using similar procedures Poly(50% PrD-diI$_2$DAT-co-50% TyLactate210 carbonate), Poly(50% PrD-diI$_2$DAT-co-50% TyLactate282 carbonate), Poly(50% PrD-diI$_2$DAT-co-50% TyLactate1500 carbonate), Poly(50% PrD-diI$_2$DAT-co-50% TyLactate4000 carbonate), and Poly(50% PrD-diI$_2$DAT-co-50% TyLactate7000 carbonate) were also prepared.

Example 7. Preparation of Poly(50% PrD-diI$_2$DAT-co-50% (Tyrosyhrimethylene Carbonate) Carbonate)

Using procedures similar those described in Example 6 substituting Tyrosyl trimethylene carbonate for tyrosyl lactate the title polymers are prepared.

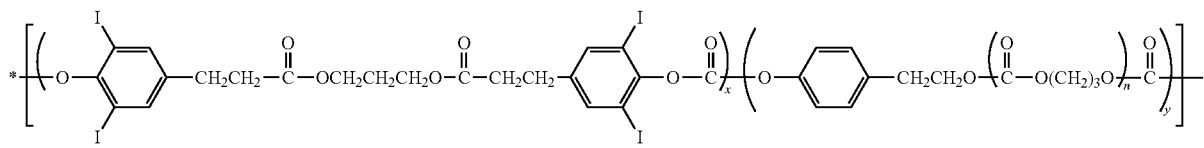

Example 8. Preparation of Poly(50% PrD-diI$_2$DAT-co-50% Tyrosylcaprolactone Carbonate)

Using procedures similar those described in Example 6 substituting Tyrosyl caprolactone for tyrosyl lactate the titled polymers are prepared.

Example 9. Synthesis of (4-(2-hydroxyethyl) 2,6,-diiodophenol)

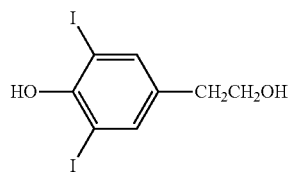

Iodination of tyrosol was carried out by adding 200 mL of KICl$_2$ solution (2M) to 27.6 g (0.2 mol) of tyrosol in 140 mL of 95% ethanol and stirring the resulting solution for 1 h. When treated with 400 mL of water, an oil separated which was stirred with 100 mL of 2% sodium thiosulfate solution for 2 h. The brown solid obtained was dissolved in ethanol and treated with charcoal and filtered. The pure diiodotyrosol (4-(2-hydroxyethyl) 2,6,-diiodophenol) was obtained in 65% yield and was characterized by hplc and NMR.

Example 10. Alternative Preparation of 12 Tyrosyl Lactate282

The compound of Example 9 is submitted to the reaction conditions of Example 1 to provide the same product as Example 3.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and scope of the invention, and all such variations are intended to be included within the scope of the following claims.

What is claimed is:

1. A hydroxyacid-phenol compound of formula:

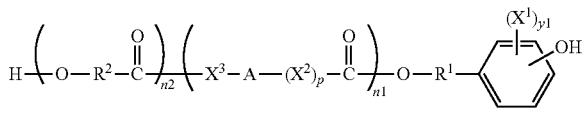

wherein
y1 is 1, 2, 3, or 4;
$X^1$ is bromine (Br) or iodine (I);
$X^2$ and $X^3$ are independently selected from O, S and NR, where R is H or lower alkyl;
$R^1$ is selected from the group consisting of linear or branched $C_1$-$C_{12}$ alkylene;
A is selected from the group consisting of linear or branched $C_1$-$C_{24}$ alkylene;
$R^2$ is selected from the group consisting of linear or branched $C_1$-$C_{24}$ alkylene;
n1 and n2 are independently numbers from 0 to 100, and are average values which can be fractional, where the sum of n1 and n2 is at least 1;
p is zero or 1, provided that when p=0, $X^1$ is I (iodine); and
wherein each said alkyl and alkylene can be independently substituted with one or more of hydroxy, alkoxy, halogen, nitro, cyano, CO$_2$H, CO$_2$-lower alkyl, phenyl, aryl, heteroaryl, cycloalkyl, mercapto, or alkylthio.

2. The hydroxyacid-phenol compound of claim 1, wherein n1 is zero and n2 is an average value of 2.

3. The hydroxyacid-phenol compound of claim 1, wherein $X^1$=I and y1=2.

4. The hydroxyacid-phenol compound of claim 1, wherein $R^1$ is —CH$_2$CH$_2$—.

5. The hydroxyacid-phenol compound of claim 1, having the formula:

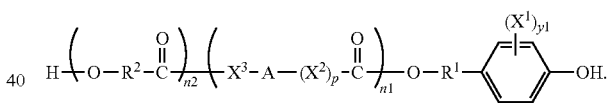

6. The hydroxyacid-phenol compound of claim 1 having the formula:

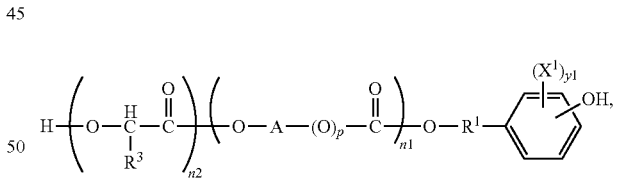

wherein $R^3$ is selected from the group consisting of hydrogen and linear or branched $C_1$-$C_{23}$ alkyl.

7. The hydroxyacid-phenol compound of claim 6 having the formula:

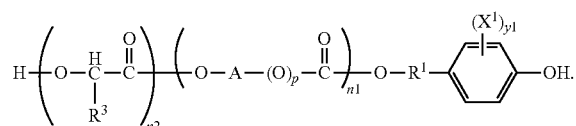

8. The hydroxyacid-phenol compound of claim 7, wherein $R^3$ is hydrogen or methyl.

9. The hydroxyacid-phenol compound of claim 7, wherein n2 is greater than zero and $R^3$ is methyl and the subunit is derived from L-lactic acid.

10. The hydroxyacid-phenol compound of claim 7, wherein n2 is greater than zero and $R^3$ is methyl and the subunit is derived from D-lactic acid.

11. The hydroxyacid-phenol compound of claim 7, wherein n2 is greater than zero and $R^3$ is methyl and the subunit is derived from D,L-lactic acid.

* * * * *